US012606846B2

(12) United States Patent
Wein et al.

(10) Patent No.: US 12,606,846 B2
(45) Date of Patent: Apr. 21, 2026

(54) MATERIALS AND METHODS FOR THE TREATMENT OF DISORDERS ASSOCIATED WITH THE IRF2BPL GENE

(71) Applicant: RESEARCH INSTITUTE AT NATIONWIDE CHILDREN'S HOSPITAL, Columbus, OH (US)

(72) Inventors: Nicolas Sebastien Wein, Columbus, OH (US); Kathrin Christine Meyer, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 951 days.

(21) Appl. No.: 17/769,933

(22) PCT Filed: Oct. 19, 2020

(86) PCT No.: PCT/US2020/056358
§ 371 (c)(1),
(2) Date: Apr. 18, 2022

(87) PCT Pub. No.: WO2021/077101
PCT Pub. Date: Apr. 22, 2021

(65) Prior Publication Data
US 2022/0389453 A1     Dec. 8, 2022

Related U.S. Application Data

(60) Provisional application No. 62/923,432, filed on Oct. 18, 2019.

(51) Int. Cl.
*C12N 15/86* (2006.01)
*C12N 15/113* (2010.01)

(52) U.S. Cl.
CPC ............ *C12N 15/86* (2013.01); *C12N 15/113* (2013.01); *C12N 2750/14143* (2013.01)

(58) Field of Classification Search
CPC .................................................. C12N 15/113
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 7,282,199 B2 | 10/2007 | Gao et al. | |
| 7,790,449 B2 | 9/2010 | Gao et al. | |

FOREIGN PATENT DOCUMENTS

| | | | | |
|---|---|---|---|---|
| JP | 2018-500311 A | 1/2018 | | |
| JP | 2019500034 A | 1/2019 | | |
| WO | 95/13365 A1 | 5/1995 | | |
| WO | 95/13392 A1 | 5/1995 | | |
| WO | 96/17947 A1 | 6/1996 | | |
| WO | 97/06243 A1 | 2/1997 | | |
| WO | 97/08298 A1 | 3/1997 | | |
| WO | 97/09441 A2 | 3/1997 | | |
| WO | 97/21825 A1 | 6/1997 | | |
| WO | 98/09657 A2 | 3/1998 | | |
| WO | 99/11764 A2 | 3/1999 | | |
| WO | 01/83692 A2 | 11/2001 | | |
| WO | WO-2016100575 A1 * | 6/2016 | ............. | A61K 48/00 |
| WO | WO-2017/106313 A1 | 6/2017 | | |
| WO | 2018/094251 A1 | 5/2018 | | |

OTHER PUBLICATIONS

Umarov, Bioinformatics, 35(16), 2019, 2730-2737.*
FitzPatrick et al., 2023, Nucleic Acids Res, 51(11):5499-5511.*
Carter, Adeno-associated virus vectors, Current Opinions in Biotechnology, 3(5):533-539 (1992).
Chao et al., Several log increase in therapeutic transgene delivery by distinct adeno-associated viral serotype vectors, Mol. Ther., 2(6):619-623 (2000).
Chao et al., Sustained and complete phenotype correction of hemophilia B mice following intramuscular injection of AAV1 serotype vectors, Mol. Ther., 4(3):217-222 (2001).
Clark et al., A stable cell line carrying adenovirus-inducible rep and cap genes allows for infectivity titration of adeno-associated virus vectors, Gene. Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
Clark et al., Recombinant adeno-associated viral vectors mediate long-term transgene expression in muscle, Hum. Gene. Ther., 8(6):659-669 (1997).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Ganos et al., IRF2BPL mutations cause autosomal dominant dystonia with anarthria, slow saccades and seizures, Park. Relat. Discord., 68(17):57-59 (2019).
Gao et al., Clades of Adeno-associated Viruses Are Widely Disseminated in Human Tissues, J. Virol., 78:6381-6388 (2004).
Heger et al., Enhanced at puberty 1 (EAPI) is a new transcriptional regulator of the female neuroendocrine reproductive axis, J. Clin. Invest., 117(8):2145-2154 (2007).

(Continued)

*Primary Examiner* — Valarie E Bertoglio

(74) *Attorney, Agent, or Firm* — MARSHALL, GERSTEIN & BORUN LLP

(57) ABSTRACT

The disclosure provides gene therapy vectors, such as adeno-associated virus (AAV), designed for treatment of an Interferon regulatory factor 2 binding protein like (IRF2BPL) disorder.

7 Claims, 22 Drawing Sheets

Specification includes a Sequence Listing.

(56)                    References Cited

OTHER PUBLICATIONS

Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).

Herzog et al., Stable gene transfer and expression of human blood coagulation factor IX after intramuscular injection of recombinant adeno-associated virus, Proc. Natl. Acad. Sci. USA, 94(11):5804-5809 (1997).

Higashimori et al., Forkhead Box F2 Suppresses Gastric Cancer through a Novel FOXF2-IRF2BPL-[beta]-Catenin Signaling Axis, Can. Res., 78(7):1643-1656 (2018).

Hu et al., Direct Conversion of Normal and Alzheimer's Disease HUman Fibroblasts into Neuronal Cells by Small Molecules, Cell Stem Cell, 17(2):204-12 (2015).

International Application No. PCT/US2020/056358, International Preliminary Report on Patentability, mailed Apr. 28, 2022.

International Application No. PCT/US2020/056358, International Search Report and Written Opinion, mailed Mar. 1, 2021.

Johnson et al., Therapeutic landscape for Batten disease: current treatments and future prospects, Nature Reviews Neurology, 15:161-178 (2019).

Kessler et al., Gene delivery to skeletal muscle results in sustained expression and systemic delivery of a therapeutic protein, Proc. Nat. Acad. Sci. USA, 93(24):14082-14087 (1996).

Laughlin et al., Cloning of infectious adeno-associated virus genomes in bacterial plasmids, Gene., 23(1):65-73 (1983).

Lebkowski et al., Adeno-associated virus: a vector system for efficient introduction and integration of DNA into a variety of mammalian cell types, Mol. Cell. Biol., 8(10:)3988-3996, (Oct. 1988).

Lewis et al., Generation of neutralizing activity against human immunodeficiency virus type 1 in serum by antibody gene transfer, J. Virol., 76(17):8769-8775 (2002).

Marcogliese et al., IRF2BPL Is Associated with Neurological Phenotypes, Am. J. Hum. Genet., 103(2):245-260 (2018).

Marcogliese et al., IRF2BPL Is Associated with Neurological Phenotypes, The American Journal of Human Genetics, 103:245-260 (2018).

Marsic et al., Vector Design Tour de Force: Integrating Combinatorial and Rational Approaches to Derive Novel Adeno-associated Virus Variants, Molecular Therapy, 22(11):1900-1909 (2014).

Mau-Them et al., De novo truncating variants in the intronless IRF2BPL are responsible for developmental epileptic encephalopathy, Genetics in Medicine, 21:1008-1014 (2019).

Mclaughlin et al., Adeno-associated virus general transduction vectors: analysis of proviral structures, J. Virol., 62(6):1963-73 (1988).

Meyer et al., Direct conversion of patient fibroblasts demonstrates non-cell autonomous toxicity of astrocytes to motor neurons in familial and sporadic ALS, PNAS, 111(2):829-832 (2014).

Mori et al., Two novel adeno-associated viruses from cynomolgus monkey: pseudotyping characterization of capsid protein, Virology, 330(2):375-383 (2004).

Murphy et al., Long-term correction of obesity and diabetes in genetically obese mice by a single intramuscular injection of recombinant adeno-associated virus encoding mouse leptin, Proc. Natl. Acad. Sci. USA, 94(25):13921-13926 (1997).

Muzyczka, Use of Adeno-Associated Virus as a General Transduction Vector for Mammalian Cells, Curr. Topics in Microbiol and Immunol., 158:97-129 (1992).

Paul et al., Increased Viral Titer Through Concentration of Viral Harvests from Retroviral Packaging Lines, Human Gene Therapy, 4(5):609-615 (1993).

Pena et al., Database of clinical data for individuals with variants in the IRF2BPL gene (IRF2BPL), XP002802117, (2019), Retrieved from the Internet: URL:https://www.clinicaltrials.gov/ct2/show/record/NCT03892798 [retrieved on Feb. 16, 2021], (2019).

Perrin et al., An experimental rabies vaccine produced with a new BHK-21 suspension cell culture process: use of serum-free medium and perfusion-reactor system, Vaccine, 13(13):1244-1250 (1995).

Rodino-Klapac et al., A translational approach for limb vascular delivery of the micro-dystrophin gene without high volume or high pressure for treatment of Duchenne muscular dystrophy, J. Transl. Med., 5:45-55 (2007).

Ruffing et al., Mutations in the carboxy terminus of adeno-associated virus 2 capsid proteins affect viral infectivity: lack of an RGD integrin-binding motif Free, J. Gen. Virol., 75:3385-3392 (1994).

Samulski et al., Cloning of adeno-associated virus into pBR322: rescue of intact virus from the recombinant plasmid in human cells, Proc. Natl. Acad. Sci. U.S.A., 79(6):2077-2081 (1982).

Samulski et al., Helper-free stocks of recombinant adeno-associated viruses: normal integration does not require viral gene expression, J. Virol., 63(9):3822-3828 (1989).

Schenpp et al., Highly purified recombinant adeno-associated virus vectors. Preparation and quantitation, Methods Mol. Med., 69:427-443 (2002).

Senapathy et al., Molecular cloning of adeno-associated virus variant genomes and generation of infectious virus by recombination in mammalian cells, J. Biol. Chem., 259:4661-4666 (1984).

Skorvanek et al., Neurodevelopmental disorder associated with IRF2BPL gene mutation: Expanding the phenotype?, Parkinsonism Relat. Disord., 62:239-241 (2019).

Srivastava et al., Nucleotide Sequence and Organization of the Adeno-Associated Virus 2 Genome, J. Virol., 45:555-564 (1983).

Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).

Tratschin et al., Adeno-associated virus vector for high-frequency integration, expression, and rescue of genes in mammalian cells, Mol. Cell. Biol., 5(11):3251-3260 (1985).

Xiao et al., Efficient long-term gene transfer into muscle tissue of immunocompetent mice by adeno-associated virus vector, J. Virol., 70(11):8098-8108 (1996).

* cited by examiner

IRF2BPL staining

IRF2BPL accumulates in the cytoplasm within patient astrocytes iAstrocytes

Dapi
IRF2BPL

Figure 5

Cytoplasm accumulation Count

NEDAMSS patients have increased expression of WNT1
Immunoflorescence assay was carried out (n=2)

DAPI/WNT1

GABA stain

P4 patient

P2 patient

H2 Control

P1 patient

Figure 14 ssAAV9-p546 pIRF$^{ENH}$-5'UTR-IRF2BPL (SEQ ID NO: 3)

AAV2 ITR nucleotides 342-482
*p546 promoter* nucleotides 534-1079
<u>pIRF$^{296}$</u> nucleotides 1154-1449
<u>5'UTR</u> nucleotides 1456-2362
<u>IRF2BPL</u> nucleotides 2363-4753
<u>BGHpA</u> nucleotides 4760-4808
AAV2 ITR nucleotides 5159-5299

GGCGAAAAACCGTCTATCAGGGCGATGGCCCACTACGTGAACCATCACCCAAATCAAGTTTTTTGGGGTCGAGGT
GCCGTAAAGCACTAAATCGGAACCCTAAAGGGAGCCCCCGATTTAGAGCTTGACGGGGAAAGCCGGCGAACGTG
GCGAGAAAGGGAAGGGAAGAAAGCGAAAGGAGCGGGCGCTAGGGCGCTGGCAAGTGTAGCGGTCACGCTGCGC
GTAACCACCACACCCGCCGCGCTTAATGCGCCGCTACAGGGCGCGTACTATGGTTGCTTTGACGTATGCGGTGTGA
AATACCGCACAGATGCGTAAGGAGAAAATACCGCATCAGGCGCCCCTGCAGGCAGCTGCGCGCTCGCTCGCTCAC
TGAGGCCGCCCGGGCAAAGCCCGGGCGTCGGGCGACCTTTGGTCGCCCGGCCTCAGTGAGCGAGCGAGCGCGC
AGAGAGGGAGTGGCCAACTCCATCACTAGGGGTTCCTGCGGCGCGGCCGC*ggtacCaaaaATcgataaaaggcgcgcca*
*aaaACGCGTGAACAACGCCAGGCTCCTCAACAGGCAACTTTGCTACTTCTACAGAAATGATAATAAAGAAATGCT*
*GGTGAAGTCAAATGCTTATCACAATGGTGAACTACTCAGCAGGGAGGCTCTAATAGGCGCCAAGAGCCTAGACTT*
*CCTTAAGCGCCAGAGTCCACAAGGGCCCAGTTAATCCTCAACATTCAAATGCTGCCCACAAAACCAGCCCCTCTGTG*
*CCCTAGCCGCCTCTTTTTTCCAAGTGACAGTAGAACTCCACCAATCCGCAGCTGAATGGGGTCCGCCTCTTTTCCCTG*
*CCTAAACAGACAGGAACTCCTGCCAATTGAGGGCGTCACCGCTAAGGCTCCGCCCCAGCCTGGGCTCCACAACCAA*
*TGAAGGGTAATCTCGACAAAGAGCAAGGGGTGGGGCGCGGGCGCGCAGGTGCAGCAGCACACAGGCTGGTCGG*
*GAGGGCGGGGCGCGACGTCTGCCGTGCGGGGTCCCGGCATCGGTTGCGCGCGCGCTCCCTCCTCTCGGAGAGAG*
*GGCTGTGGTAAAACCCGTCCGGAAAACGCGTCGAAGGGCGAATTCTGCAGATAACTGGTAAGTTTAGTCT*<u>TTTTTG</u>
<u>TCTTTTATTTCAGGTCCCGGATCC</u>GGAAAGGAAAGGTCATCGTCTGTTTAATTTCCACCCCCAGCTCTGGACTTCCA
GCATTAGCTCGCCGGGCCTCAGCTGTTGTACACACACGGCGAGGGGGGAGGGGAGGGCGGAGGCGCGGAGGA
GGGGCCGGCTGGGAGGAATCTGGGCGTCCTGCCGCGCATGCGCCTTGCCTGAGCAACAAGTGGGCTCCACAGAG
GAAGTGTAAAGGGGAGGGGGAAGAACTGGTGCAGAGCATGGCGGTGACGTCAGCGCTCCGCCCGGGCGGCATC
CCGCGCGGCCAAGCCGGGGACAGC*accggtgcgagccgcagccggagcaggagcgccgagacgcgcctccggaacgtagagtaacaa*
*tcacaacccacattccgggcgagcgtgagcacgagcgggaagggatgcgacccgggccgagcgccgcgcgagcgccctgcagccaacgtgagc*
*gccgccagccgcggcggcccgggcgccggccaggcctggggcggcggggagcctgcgtgcgtgcactcctctcctctgctctcgtgcgtcctggaagc*
*agtggccgcggcggctccctccggggtgcaaacccagtcgccgccagcagaacggccgacgctgcggaggggagaaggtcctttctcggctgccacc*
*ccctcccccggtcctccggggaagcagcggcttcagcaagattggacccgggcaccgggtggcactgaaccctctggccctcgccccagggggcccg*
*tcggggagaggacgcagctcgtaggggggtccccggggagaggaagagacagcccctttcgagcttccacgcaccagccactccggggagggggc*
*caagaggcaacggcggccaccaccgggcaccctcgcccctcccctcgggccgggagcttccagcccaagtctgcagcaccaggaagaaggcgcct*
*gagctccctcgcgacgagtcaaccgcagtaggaggtggggcgaagagaggctgaaccgtccgctgcccggcggtggagcccccacggcga*
*ggcgctgcgccggcggtggagactcgcgttcctccagcccctggggcagaactttctcgcccccccctcctccctccccgcagtcggactccctcccca*
*gccggccagtcctcccggaggagaaggcgccgcggagacagcccggcgggggcctaccttccccagggcaggcatcatgtcggcggcgcaggtgt*
*cctcgtcccggagacaatcttgctacctgtgcgacctgccccgcatgccctgggccatgatctgggacttctcggaacccgtatgccgcggttgcgtca*
*actacgagggcgctgatcgcatcgaattcgtgatcgagacagcgcgccagctgaaagcgggcgcacggctgcttccaggacggccgctccccgggc*
*cgccgccgcccgtcggggtcaagacagtggccctgtcggctaaggaagcggcggcggcggccagcagcggcggccgccgccgccgccgcgcaa*
*cagcaacagcaacagcagcagcagcagcaacagcagcagcagcagcagcagcagcagcaacaacagctcaaccacgttgatggttcc*
*agcaagcctgcggtgctggcggcccccgtctggcctggagcgctacggcctaagcgctgccgccgccgccgccgccgccgccgccgctgcggtggaac*
*agcgcagccgcttcgagtacccgccaccgccggtgagcctgggaagcagcagccacaccgcgcgactgcccaacggcctgggggggcccaaacggc*
*ttccccaaaccaacaccagaggagggaccccagagctgaaccgtcagagccccaattcttcttcagcggcggcgtcggtggcgtctcggcgtgga*
*acgcacggtgggctggttacggggctgcccaacccggggggtggcggaggccccagctcaccgtgccccccaacctgctaccgcagacgctgctt*

Figure 14 Continued aacggcccggccagcgctgcggtactcccccaccccctccccacgccctgggcagccgtgggcccccgacgcctgctcccccagggggctcctgggg gccccgccttgtctcggggggtaccccgggtgtatcggccacgtcgtcctccgcgtcgtcttcgacctcttcgtcggtggcagaggtgggcgtgggtgctg gtggtaagagagcccggctcggtgtcgagcacagaccaggagcgcgagttgaaggagaagcagcgcaacgccgaggccctggccgagctgagcga gagcctgcgcaaccgcgccgaggagtgggccagcaagcccaagatggtccgcgacacgctgctcacgctggcaggctgcacgccctacgaggttc gcttcaagaaggaccactcgctgctgggccgcgttttcgccttcgacgccgtctccaagcccggcatggactacgaattgaagctgttcattgagtac cccacgggctcgggcaacgtgtactccagtgcatctggtgtggccaagcagatgtatcaggactgcatgaaggacttcggccgggggcctatcctcgg gtttcaagtacctggagtacgaaaagaagcacggctccggggactggcgcctgcttggagacctgctccccgaagccgtgcgcgcttcttcaaggagg gcgtgcccggccgccgacatgctgccccagccctacctggacgccagctgtcccatgctgcccactgctctggtgagtctgagccgcgcccccagcgca ccccgggggaccggggccttgccgcccgccgcggccgtcgggccgggggcgcagccgccagcctgcgcaagagaaaggcctctccggagccccggga ctcagccgagggcgcgctgaagctgggcgaggaacagcagaggcagcagtggatggcgaaccagagcgaggcgctgaagctcaccatgtccgcc gggggcttcgcggcgccggggcacgcggcgggggggtccgcctccgccgccccacctctgggacccattccaaccggaccacccccacctgagtcag ccccccagaacggtccgtcccctatggccgctctcatgtcggtggcagatactctgggcacagccgcactcgcccaaggatggcagttccgtgcactct accactgcgtcggcgcggcgaaacagcagcagcccagtctcgccggcctccgtgccggggcagcgccgcttggcatcacgtaacggggacctgaat ttacaggtggcgccccgccgcctagcgcccacccgggcatggaccaagtgcacccccaaaacattccggattcccccatggccaacagcggaccc ctctgctgcaccatttgccacgaacgtttggaggatacgcatttcgttcagtgcccttccgtccccagccacaaattttgcttccttgctctagagaga gtatcaaggcccaggggggccaccggcgaggtgtattgccccagcggagagaaatgccccctagtcgggtcgaatgtaccttgggccttcatgcagg gcgaaatcgcgactatcttagctggggatgttaaagtgaaaaaggagagagacccttgaaagcttAATAAAAGATCTTTATTTTTCATTAG ATCTGTGTGTTGGTTTTTTTGTGTGaaacTCGAGaaGATATCaaCTGCCTTCTACTGGGCGGTTTTATGGACAGCAAGC

GAACCGGAATTGCCAGCTGGGGCGCCCTCTGGTAAGGTTGGGAAGCCCTGCAAAGTAAACTGGATGGCTTTCTCG

CCGCCAAGGATCTGATGGCGCAGGGGATCAAGCTCTGATCAAGAGACAGGATGAGGATCGTTTCGCGTTCTTGAC

TCTTCGCGATGTACGGGCCAGATATACGCGTTGACATTGATTATTGACTAGTTATTAATAGTAATCAATTACGGGG

TCATTAGTTCATAGCCCATATATGGAGTTCCGcTCGAGCaaaggcgcgccaaaaaaGcatgcGGCCGCGCAGGAACCCCT

AGTGATGGAGTTGGCCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGCCTGCAGGACATGtgagcaaaaggcca gcaaaaggccaggaaccgtaaaaaggccgcgttgctggcgtttttccataggctccgcccccctgacgagcatcacaaaaatcgacgctcaagtcag aggtggcgaaacccgacaggactataaagataccaggcgtttccccctggaagctccctcgtgcgctctcctgttccgaccctgccgcttaccggatac ctgtccgcctttctcccttcgggaagcgtggcgctttctcatagctcacgctgtaggtatctcagttcggtgtaggtcgttcgctccaagctgggctgtgtg cacgaaccccccgttcagcccgaccgctgcgccttatccggtaactatcgtcttgagtccaacccggtaagacacgacttatcgccactggcagcagcc actggtaacaggattagcagagcgaggtatgtaggcggtgctacagagttcttgaagtggtggcctaactacggctacactagaagaacagtatttgg tatctgcgctctgctgaagccagttaccttcggaaaaagagttggtagctcttgatccggcaaacaaaccaccgctggtagcggtggtttttttgtttgc aagcagcagattacgcgcagaaaaaaaggatctcaagaagatcctttgatcttttctacggggtctgacgctcagtggaacgaaaactcacgttaag ggattttggtcatgagattatcaaaaaggatcttcacctagatcctttttaaattaaaaatgaagttttaaatcaatctaaagtatatatgagtaaacttg gtctgacagttagaaaaactcatcgagcatcaaatgaaactgcaatttattcatatcaggattatcaataccatattttgaaaaagccgtttctgtaat gaaggagaaaactcaccgaggcagttccataggatggcaagatcctggtatcggtctgcgattccgactcgtccaacatcaatacaacctattaatttc ccctcgtcaaaaataaggttatcaagtgagaaatcaccatgagtgacgactgaatccggtgagaatggcaaaagtttatgcatttctttccagacttgt tcaacaggccagccattacgctcgtcatcaaaatcactcgcatcaaccaaaccgttattcattcgtgattgcgcctgagcgaggcgaaatacgcgatc gctgttaaaaggacaattacaaacaggaatcgagtgcaaccggcgcaggaacactgccagcgcatcaacaatattttcacctgaatcaggatattctt ctaatacctggaacgctgtttttccggggatcgcagtggtgagtaaccatgcatcatcaggagtacggataaaatgcttgatggtcggaagtggcata aattccgtcagccagttagtctgaccatctcatctgtaacatcattggcaacgctacctttgccatgtttcagaaacaactctggcgcatcgggcttccc atacaagccgatagattgtcgcacctgattgcccgacattatcgcgagcccatttatacccatataaatcagcatccatgttggaatttaatcgcggcctc gacgtttcccgttgaatatggctcatactcttcctttttcaatattattgaagcatttatcagggttattgtctcatgacattaacctataaaaataggcgta tcacgaggccctttcgtctcgcgcgtttcggtgatgacggtgaaaacctctgacacatgcagctcccggagacggtcacagcttgtctgtaagcggatg ccgggagcagacaagcccgtcagggcgcgtcagcgggtgttggcgggtgtcggggctggcttaactatgcggcatcagagcagattgtacTGAGA

GTGCACCATAAAAATTGTAAACGTTAATATTTTGTTAAAATTCGCGTTAAATTTTTGTTAAATCAGCTCATTTTTTAAC

CAATAGGCCGAAATCGGCAAAATCCCTTATAAATCAAAAGAATAGCCCGAGATAGGGTTGAGTGTTGTTCCAGTTT

GGAACAAGAGTCCACTATTAAAGAACGTGGACTCCAACGTCAAAG

Figure 15 ssAAV9-pSHORT-5'UTR-IRF2BPL (SEQ ID NO: 4)

AAV2 ITR nucleotides 342-482
pSHORT[648] nucleotides 534-1182
5'UTR nucleotides 1188-2094
IRF2BPL nucleotides 2095-4985
BGHpA nucleotides 4492-4540
AAV2 ITR nucleotides 4891-5031

GGCGAAAAACCGTCTATCAGGGCGATGGCCCACTACGTGAACCATCACCCAAATCAAGTTTTTTGGGGTCGAGGT
GCCGTAAAGCACTAAATCGGAACCCTAAAGGGAGCCCCCGATTTAGAGCTTGACGGGGAAAGCCGGCGAACGTG
GCGAGAAAGGAAGGGAAGAAAGCGAAAGGAGCGGGCGCTAGGGCGCTGGCAAGTGTAGCGGTCACGCTGCGC
GTAACCACCACACCCGCCGCGCTTAATGCGCCGCTACAGGGCGCGTACTATGGTTGCTTTGACGTATGCGGTGTGA
AATACCGCACAGATGCGTAAGGAGAAAATACCGCATCAGGCGCCCCTGCAGGCAGCTGCGCGCTCGCTCGCTCAC
TGAGGCCGCCCGGGCAAAGCCCGGGCGTCGGGCGACCTTTGGTCGCCCGGCCTCAGTGAGCGAGCGAGCGCGC
AGAGAGGGAGTGGCCAACTCCATCACTAGGGGTTCCTGCGGCGCGGCCGCggtacCaaaaATcgataaaaggcgcgcca
aaaACGCGT<u>GGTTCCTAGATCAGGGCACAAAAACAAATAGAAAAGACAATTTCTGGAAGATTGGAAAACAGCTAA</u>
<u>TTTTGCAGGTGCTTCGGCATCAGTGGTGGCGATGAATTTAACATCCATGCCGGGCGGGATAAGGTTCAACCGCAG</u>
<u>ATGAAATGGTTAATACCTTATACGAAATTCACGGCGAAAAATCCTGAAACAGGACATTTAAATTCACTGCCGAGGC</u>
<u>TTGGGGGTGGGGTGGGGAGCAGGGATCGGAAACGACGCTAGTGGTTCTTAAATGCGTTTTTACTTGGGAATGCC</u>
<u>CGGCAGGGAAAGGAAAGGTCATCGTCTGTTTAATTTCCACCCCCAGCTCTGGACTTCCAGCATTAGCTCGCCGGGC</u>
<u>CTCAGCTGTTGTACACACACGGCGAGGGGGGAGGGGAGGGCGGAGGCGCGGAGGAGGGGCCGGCTGGGAGGA</u>
<u>ATCTGGGCGTCCTGCCGCGCATGCGCCTTGCCTGAGCAACAAGTGGGCTCCACAGAGGAAGTGTAAAGGGGAGG</u>
<u>GGGAAGAACTGGTGCAGAGCATGGCGGTGACGTCAGCGCTCCGCCCGGGCGGCATCCCGCGCGGCCAAGCCGG</u>
<u>GGACAGCGCGAGCCGCAGCCGGAGCAGGAGCGCCGAGACGCGCCTCCGGAACG</u>TAGAGTAACaccggtgcgagccg
cagccggagcaggagcgccgagacgcgcctccggaacgtagagtaacaatcacaaccccacattccgggcgagcgtgagcacgagcgggaaggg
atgcgacccgggccgaggcgccgcgcgagcgccctgcagccaacgtgagcgccgccagccgcggcggcccgggcgccggccagcctgggggcgg
cgggagcctgcgtgcgtgcactcctctcctctgctctcgtgcgtcctggaagcagtggccgcggcggctccctccggggtgcaaacccagtcgccgcca
gcagaacggccgacgctgcggaggggagaaggtcctttctcggctgccacccctcccccggtcctccggggaagcagcggcttcagcaagattgga
cccgggcaccgggtggcactgaaccctctggccctcgccccagggggcccgtcggggagaggacgcagctcgtaggggggtcccgggggagagga
agagacagcccctttcgagcttccacgcaccagccactccggggaggggggccaagaggcaacggcggccaccaccgggcaccctcgccccctcccct
cgggccgggagcttccagcccaagtctgcagcaccaggaagaaggcgcctgagctcccctcgcgacgagtcaaccgcagtaggaggtggggcga
agagagggctgaacccgtccgctgcccgggcggtggagcccccacggcgaggcgctgcgccggcggtggagactcgcgttccctccagcccctgggg
cagaactttctcgccccccctcctccctcccccgcagtcggactccctccccagccggccagtcctcccggaggagaaggcgccgcggagacagcccg
ggcggggcctaccttccccagggcaggcatcatgtcggcggcgcaggtgtcctcgtcccggagacaatcttgctacctgtgcgacctgccccgcatg
ccctgggccatgatctgggacttctcggaacccgtatgccgcggttgcgtcaactacgagggcgctgatcgcatcgaattcgtgatcgagacagcgc
gccagctgaagcgggcgcacggctgcttccaggacggccgctcccccgggccgccgccgcccgtcggggtcaagacagtggccctgtcggctaagg
aagcggcggcggcggcggcagcagcggcggccgccgccgccgcggcaacagcaacagcaacagcagcagcagcagcagcaacagcagcagc
agcagcagcagcagcagcagcaacaacagctcaaccacgttgatggttccagcaagcctgcggtgctggccggccccgtctggcctggagcgctacg
gcctaagcgctgccgccgccgccgccgccgccgctgcggtggaacagcgcagccgcttcgagtaccgccaccgccggtgagcctgggaa
gcagcagccacaccgcgcgactgcccaacggcctggggggcccaaacggcttccccaaaccaacaccagaggaggggacccccagagctgaaccg
tcagagccccaattcttcttcagcggcggcggcgtcggtggcgtctcggcgtggaacgcacggtgggctggttacggggctgcccaacccgggggggtggc
ggaggcccccagctcaccgtgcccccccaacctgctaccgcagacgctgcttaacggcccggccagcgctgcggtactcccccccaccccctccccacgc
cctgggcagccgtgggcccccgacgcctgctcccccaggggctcctggggggccccgcttgtctcggggggtaccccgggtgtatcggccacgtcgtcct
ccgcgtcgtcttcgacctcttcgtcggtggcagaggtgggcgtgggtgctggtggtaagagggcccggctcggtgtcgagcacagaccaggagcgcga

Figure 15 Continued gttgaaggagaagcagcgcaacgccgaggccctggccgagctgagcgagagcctgcgcaaccgcgccgaggagtgggccagcaagcccaagat
ggtccgcgacacgctgctcacgctggcaggctgcacgccctacgaggttcgcttcaagaaggaccactcgctgctgggccgcgttttcgccttcgacg
ccgtctccaagcccggcatggactacgaattgaagctgttcattgagtaccccacgggctcgggcaacgtgtactccagtgcatctggtgtggccaa
gcagatgtatcaggactgcatgaaggacttcggccggggcctatcctcgggtttcaagtacctggagtacgaaaagaagcacggctccggggactg
gcgcctgcttggagacctgctccccgaagccgtgcgcttcttcaaggagggcgtgcccggcgccgacatgctgccccagccctacctggacgccagct
gtcccatgctgcccactgctctggtgagtctgagccgcgcgccccagcgcaccccgggggaccggggccttgccgcccgccgccgccgtcgggccgggg
cgcagccgccagcctgcgcaagagaaaggcctctccggagcccccggactcagccgagggcgcgctgaagctgggcgaggaacagcagaggcag
cagtggatggcgaaccagagcgaggcgctgaagctcaccatgtccgccggggggcttcgcggcgccggggcacgcggcggggggtccgcctccgcc
gcccccacctctgggacccccattccaaccggaccacccccacctgagtcagcccccccagaacggtccgtcccctatggccgctctcatgtcggtggcag
atactctgggcacagcgcactcgcccaaggatggcagttccgtgcactctaccactgcgtcggcgcggcgaaacagcagcagcccagtctcgccgg
cctccgtgccgggcagcgccgcttggcatcacgtaacggggacctgaatttacaggtggcgcccccgccgcctagcgcccacccgggcatggacca
agtgcaccccaaacattccggattccccatggccaacagcggacccctctgctgcaccatttgccacgaacgtttggaggatacgcatttcgttc
agtgcccttccgtccccagccacaaattttgcttcccttgctctagagagagtatcaaggcccaggggggccaccggcgaggtgtattgcccagcgga
gagaaatgcccctagtcgggtcgaatgtaccttgggccttcatgcagggcgaaatcgcgactatcttagctggggatgttaaagtgaaaaaggag
agagacccttgaaagcttAATAAAGATCTTTATTTTCATTAGATCTGTGTGTTGGTTTTTTGTGTGaaacTCGAGaaGATA
TCaaCTGCCTTCTACTGGGCGGTTTTATGGACAGCAAGCGAACCGGAATTGCCAGCTGGGGCGCCCTCTGGTAAG
GTTGGGAAGCCCTGCAAAGTAAACTGGATGGCTTTCTCGCCGCCAAGGATCTGATGGCGCAGGGGATCAAGCTCT
GATCAAGAGACAGGATGAGGATCGTTTCGCGTTCTTGACTCTTCGCGATGTACGGGCCAGATATACGCGTTGACA
TTGATTATTGACTAGTTATTAATAGTAATCAATTACGGGGTCATTAGTTCATAGCCCATATATGGAGTTCCGcTCGA
GCaaaggcgcgccaaaaaaGcatgcGGCCGCGCAGGAACCCCTAGTGATGGAGTTGGCCACTCCCTCTCTGCGCGCTCG
CTCGCTCACTGAGGCCGGGCGACCAAAGGTCGCCCGACGCCCGGGCTTTGCCCGGGCGGCCTCAGTGAGCGAGC
GAGCGCGCAGCTGCCTGCAGGACATGtgagcaaaaggccagcaaaaggccaggaaccgtaaaaaggccgcgttgctggcgtttttcca
taggctccgcccccctgacgagcatcacaaaaatcgacgctcaagtcagaggtggcgaaacccgacaggactataaagataccaggcgtttccccct
ggaagctccctcgtgcgctctcctgttccgaccctgccgcttaccggatacctgtccgcctttctcccttcgggaagcgtggcgctttctcatagctcacgc
tgtaggtatctcagttcggtgtaggtcgttcgctccaagctgggctgtgtgcacgaaccccccgttcagcccgaccgctgcgccttatccggtaactatc
gtcttgagtccaacccggtaagacacgacttatcgccactggcagcagccactggtaacaggattagcagagcgaggtatgtaggcggtgctacaga
gttcttgaagtggtggcctaactacggctacactagaagaacagtatttggtatctgcgctctgctgaagccagttaccttcggaaaaagagttggtag
ctcttgatccggcaaacaaaccaccgctggtagcggtggtttttttgtttgcaagcagcagattacgcgcagaaaaaaaggatctcaagaagatccttt
gatcttttctacggggtctgacgctcagtggaacgaaaactcacgttaagggattttggtcatgagattatcaaaaaggatcttcacctagatccttta
aattaaaaatgaagttttaaatcaatctaaagtatatatgagtaaacttggtctgacagttagaaaaactcatcgagcatcaaatgaaactgcaattta
ttcatatcaggattatcaataccatattttgaaaaagccgtttctgtaatgaaggagaaaactcaccgaggcagttccataggatggcaagatcctgg
tatcggtctgcgattccgactcgtccaacatcaatacaacctattaatttcccctcgtcaaaaataaggttatcaagtgagaaatcaccatgagtgacg
actgaatccggtgagaatggcaaaagtttatgcatttctttccagacttgttcaacaggccagccattacgctcgtcatcaaaatcactcgcatcaacca
aaccgttattcattcgtgattgcgcctgagcgaggcgaaatacgcgatcgctgttaaaaggacaattacaaacaggaatcgagtgcaaccggcgcag
gaacactgccagcgcatcaacaatattttcacctgaatcaggatattcttctaatacctggaacgctgtttttccggggatcgcagtggtgagtaaccat
gcatcatcaggagtacggataaaatgcttgatggtcggaagtggcataaattccgtcagccagtttagtctgaccatctcatctgtaacatcattggca
acgctacctttgccatgtttcagaaacaactctggcgcatcgggcttcccatacaagcgatagattgtcgcacctgattgcccgacattatcgcgagccc
atttatacccatataaatcagcatccatgttggaatttaatcgcggcctcgacgtttcccgttgaatatggctcatactcttccttttcaatattattgaag
catttatcagggttattgtctcatgacattaacctataaaaataggcgtatcacgaggccctttcgtctcgcgcgtttcggtgatgacggtgaaaacctct
gacacatgcagctcccggagacggtcacagcttgtctgtaagcggatgccgggagcagacaagcccgtcagggcgcgtcagcgggtgttggcgggtg
tcggggctggcttaactatgcggcatcagagcagattgtacTGAGAGTGCACCATAAAATTGTAAACGTTAATATTTTGTTAAAAT
TCGCGTTAAATTTTTGTTAAATCAGCTCATTTTTTTAACCAATAGGCCGAAATCGGCAAAATCCCTTATAAATCAAAA
GAATAGCCCGAGATAGGGTTGAGTGTTGTTCCAGTTTGGAACAAGAGTCCACTATTAAAGAACGTGGACTCCAAC
GTCAAAG

Figure 16 ssAAV9-p546-5'UTR-IRF2BPL (SEQ ID NO: 7)

AAV2 ITR nucleotide 342 - 482
*p546 promoter* nucleotides 534-1079
5'UTR nucleotides 1227-2133
IRF2BPL nucleotides 2134-4524
BGHpA nucleotides 4531-4579
AAV2 ITR nucleotides 4930-5070

GGCGAAAAACCGTCTATCAGGGCGATGGCCCACTACGTGAACCATCACCCAAATCAAGTTTTTTGGGGTCGAGGT
GCCGTAAAGCACTAAATCGGAACCCTAAAGGGAGCCCCCGATTTAGAGCTTGACGGGGAAAGCCGGCGAACGTG
GCGAGAAAGGAAGGGAAGAAAGCGAAAGGAGCGGGCGCTAGGGCGCTGGCAAGTGTAGCGGTCACGCTGCGC
GTAACCACCACACCCGCCGCGCTTAATGCGCCGCTACAGGGCGCGTACTATGGTTGCTTTGACGTATGCGGTGTGA
AATACCGCACAGATGCGTAAGGAGAAAATACCGCATCAGGCGCCCCTGCAGGCAGCTGCGCGCTCGCTCGCTCAC
TGAGGCCGCCCGGGCAAAGCCCGGGCGTCGGGCGACCTTTGGTCGCCCGGCCTCAGTGAGCGAGCGAGCGCGC
AGAGAGGGAGTGGCCAACTCCATCACTAGGGGTTCCTGCGGCGCGGCCGCggtacCaaaaATcgataaaaggcgcgcca
aaaACGCGT*GAACAACGCCAGGCTCCTCAACAGGCAACTTTGCTACTTCTACAGAAAATGATAATAAAGAAATGCT*
*GGTGAAGTCAAATGCTTATCACAATGGTGAACTACTCAGCAGGGAGGCTCTAATAGGCGCCAAGAGCCTAGACTT*
*CCTTAAGCGCCAGAGTCCACAAGGGCCCAGTTAATCCTCAACATTCAAATGCTGCCCACAAAACCAGCCCCTCTGTG*
*CCCTAGCCGCCTCTTTTTTCCAAGTGACAGTAGAACTCCACCAATCCGCAGCTGAATGGGGTCCGCCTCTTTTCCCTG*
*CCTAAACAGACAGGAACTCCTGCCAATTGAGGGCGTCACCGCTAAGGCTCCGCCCCAGCCTGGGCTCCACAACCAA*
*TGAAGGGTAATCTCGACAAAGAGCAAGGGGTGGGGCGCGGGCGCGCAGGTGCAGCAGCACACAGGCTGGTCGG*
*GAGGGCGGGGCGCGACGTCTGCCGTGCGGGGTCCCGGCATCGGTTGCGCGCGCGCTCCCTCCTCTCGGAGAGAG*
*GGCTGTGGTAAAACCCGTCCGGAAAACGCGTCGAAGGGCGAATTCTGCAGATAACTGGTAAGTTTAGTC*TTTTTTG
TCTTTTATTTCAGGTCCCGGATCCGGTGGTGGTGCAAATCAAAGAACTGCTCCTCAGTCGATGTTGCCTTTACTTCT
AGGCCTGTACGGAAaccggtgcgagccgcagccggagcaggagcgccgagacgcgcctccggaacgtagagtaacaatcacaaccccacat
tccgggcgagcgtgagcacgagcgggaagggatgcgacccgggccgaggcgccgcgcgagcgccctgcagccaacgtgagcgccgccagccgcgg
cggcccggcgccggccaggcctggggcggcggcggagcctgcgtgcgtgcactcctctcctctgctctcgtgcgtcctggaagcagtggccgcggcgg
ctccctccggggtgcaaacccagtcgccgccagcagaacggccgacgctgcggaggggagaaggtcctttctcggctgccaccccctcccccggtcct
ccgaggaagcagcggcttcagcaagattggacccgggcaccgggtggcactgaaccctctggccctcgccccagggggcccgtcggggagaggacg
cagctcgtaggggggtccccggggagaggaagagacagcccctttcgagcttccacgcaccagccactccggggaggggggccaagaggcaacggc
ggccaccaccgggcaccctcgcccctcccctcgggccgggagcttccagcccaagtctgcagcaccaggaagaaggcgcctgagctccctcgcga
cgagtcaaccgcagtaggagagtgggggcgaagagagggctgaacccgtccgctgcccgggcggtggagcccccacggcgaggcgctgcgccggcg
gtggagactcgcgttccctccagccctgggcagaactttctcgcccccccctcctccctcccccgcagtcggactccctccccagccggccagtcctcc
cggaggagaaggcgccgcggagacagcccggcggggcctaccttccccagggcaggcatcatgtcggcggcgcaggtgtcctcgtcccggaga
caatcttgctacctgtgcgacctgccccgcatgccctgggccatgatctgggacttctcggaacccgtatgccgcggttgcgtcaactacgagggcgct
gatcgcatcgaattcgtgatcgagacagcgcgccagctgaagcgggcgcacggctgcttccaggacggccgctcccccgggccgccgccgccgccgtc
ggggtcaagacagtggccctgtcggctaaggaagcggcggcggcggcggcagcagcggcggccgccgccgccgccgcgcaacagcaacagcaac
agcagcagcagcagcagcaacagcagcagcagcagcagcagcaacagcaacaacagctcaaccacgttgatggttccagcaagcctgcggt
gctggcggccccgtctgtcctggagcgctacggccctaagcgctgccgccgccgccgccgccgccgccgccgccgccgcctgcggtggaacagcgcagccgcttc
gagtacccgccaccgccggtgagcctgggaagcagcagccacaccgcgcgactgcccaacggcctgggggggcccaaacggcttccccaaaccaac
accagaggaggggacccccagagctgaaccgtcagagccccaattcttcttcagcggcggcgtcggtggcgtctcggcgtggaacgcacggtgggct
ggttacggggctgcccaacccgggggggtggcggaggcccccagctcaccgtgcccccaacctgctaccgcagacgctgcttaacggcccggccag
cgctgcggtactcccccacccccctcccacgccctgggcagccgtgggcccccgacgcctgctcccccagggggctcctgggggcccccgcttgtctcgg
gggtaccccgggtgtatcggccacgtcgtcctccgcgtcgtcttcgacctcttcgtcggtggcagaggtgggcgtgggtgctggtggtaagagcccg
gctcggtgtcgagcacagaccaggagcgcgagttgaaggagaagcagcgcaacgccgaggccctggccgagctgagcgagagcctgcgcaaccg

Figure 16 Continued cgccgaggagtgggccagcaagcccaagatggtccgcgacacgctgctcacgctggcaggctgcacgccctacgaggttcgcttcaagaaggacc actcgctgctgggccgcgttttcgccttcgacgccgtctccaagcccggcatggactacgaattgaagctgttcattgagtaccccacgggctcgggc aacgtgtactccagtgcatctggtgtggccaagcagatgtatcaggactgcatgaaggacttcggccgggccctatcctcgggtttcaagtacctgg agtacgaaaagaagcacggctccggggactggcgcctgcttggagacctgctccccgaagccgtgcgcttcttcaaggagggcgtgcccggcgccg acatgctgccccagccctacctggacgccagctgtcccatgctgcccactgctctggtgagtctgagccgcgcgccccagcgcaccccgggggaccggg gccttgccgcccgccgcgcgccgtcgggccggggcgcagccgccagcctgcgcaagagaaaggcctctccggagcccccggactcagccgagggcgc gctgaagctgggcgaggaacagcagaggcagcagtggatggcgaaccagagcgaggcgctgaagctcaccatgtccgccggggccttcgcggcg ccggggcacgcggcggggggtccgcctccgccgccccacctctgggaccccattccaaccggaccaccccacctgagtcagcccccccagaacggtc cgtcccctatggccgctctcatgtcggtggcagatactctgggcacagcgcactcgcccaaggatggcagttccgtgcactctaccactgcgtcggcg cggcgaaacagcagcagcccagtctcgccggcctccgtgccggggcagcgccgcttggcatcacgtaacggggacctgaatttacaggtggcgccc ccgccgcctagcgcccacccgggcatggaccaagtgcacccccaaaacattccggattccccatggccaacagcggacccctctgctgcaccattt gccacgaacgtttggaggatacgcatttcgttcagtgcccttccgtccccagccacaaattttgcttcccttgctctagagagagtatcaaggcccagg gggccaccggcgaggtgtattgccccagcggagagaaatgccccctagtcgggtcgaatgtaccttgggccttcatgcaggcgaaatcgcgacta tcttagctggggatgttaaagtgaaaaaggagagagagacccttgaaagctt<u>AATAAAAGATCTTTATTTTCATTAGATCTGTGTGTTG</u>

<u>GTTTTTTGTGTG</u>aaacTCGAGaaGATATCaaCTGCCTTCTACTGGGCGGTTTTATGGACAGCAAGCGAACCGGAATT

GCCAGCTGGGGCGCCCTCTGGTAAGGTTGGGGAAGCCCTGCAAAGTAAACTGGATGGCTTTCTCGCCGCCAAGGAT

CTGATGGCGCAGGGGATCAAGCTCTGATCAAGAGACAGGATGAGGATCGTTTCGCGTTCTTGACTCTTCGCGATG

TACGGGCCAGATATACGCGTTGACATTGATTATTGACTAGTTATTAATAGTAATCAATTACGGGGTCATTAGTTCAT

AGCCCATATATGGAGTTCCGcTCGAGCaaaggcgcgccaaaaaaGcatgcGGCCGCGCAGGAACCCCTAGTGATGGAGT

TGGCCACTCCCTCTCTGCGCGCTCGCTCGCTCACTGAGGCCGGGCGACCAAAGGTCGCCCGACGCCCGGGCTTTG

CCCGGGCGGCCTCAGTGAGCGAGCGAGCGCGCAGCTGCCTGCAGGACATGtgagcaaaaggccagcaaaaggccaggaa ccgtaaaaaggccgcgttgctggcgtttttccataggctccgcccccctgacgagcatcacaaaaatcgacgctcaagtcagaggtggcgaaacccga caggactataaagataccaggcgtttccccctggaagctccctcgtgcgctctcctgttccgaccctgccgcttaccggatacctgtccgcctttctccct tcgggaagcgtggcgctttctcatagctcacgctgtaggtatctcagttcggtgtaggtcgttcgctccaagctgggctgtgtgcacgaaccccccgttc agcccgaccgctgcgccttatccggtaactatcgtcttgagtccaacccggtaagacacgacttatcgccactggcagcagccactggtaacaggatt agcagagcgaggtatgtaggcggtgctacagagagttcttgaagtggtggcctaactacggctacactagaagaacagtatttggtatctgcgctctgctg aagccagttaccttcggaaaaagagttggtagctcttgatccggcaaacaaaccaccgctggtagcggtggtttttttgtttgcaagcagcagattacg cgcagaaaaaaaggatctcaagaagatcctttgatcttttctacggggtctgacgctcagtggaacgaaaactcacgttaagggattttggtcatgag attatcaaaaaggatcttcacctagatcctttaaattaaaaatgaagttttaaatcaatctaaagtatatatgagtaaacttggtctgacagttagaaa aactcatcgagcatcaaatgaaactgcaatttattcatatcaggattatcaataccatattttgaaaaagccgtttctgtaatgaaggagaaaactca ccgaggcagttccataggatggcaagatcctggtatcggtctgcgattccgactcgtccaacatcaatacaacctattaatttcccctcgtcaaaaata aggttatcaagtgagaaatcaccatgagtgacgactgaatccggtgagaatggcaaaagtttatgcatttctttccagacttgttcaacaggccagcca ttacgctcgtcatcaaaatcactcgcatcaaccaaaccgttattcattcgtgattgcgcctgagcgaggcgaaatacgcgatcgctgttaaaaggacaa ttacaaacaggaatcgagtgcaaccggcgcaggaacactgccagcgcatcaacaatattttcacctgaatcaggatattcttctaataccctggaacgc tgttttccgggggatcgcagtggtgagtaaccatgcatcatcaggagtacggataaaatgcttgatggtcggaagtggcatataaattccgtcagccagtt tagtctgaccatctcatctgtaacatcattggcaacgctacctttgccatgtttcagaaacaactctggcgcatcgggcttcccatacaagcgatagatt gtcgcacctgattgcccgacattatcgcgagcccatttatacccatataaatcagcatccatgttggaatttaatcgcggcctcgacgtttcccgttgaat atggctcatactcttcctttttcaatattattgaagcatttatcagggtttattgtctcatgacattaacctataaaaataggcgtatcacgaggcccttcg tctcgcgcgtttcggtgatgacggtgaaaacctctgacacatgcagctcccggagacggtcacagcttgtctgtaagcggatgccgggagcagacaag cccgtcagggcgcgtcagcgggtgttggcgggtgtcggggctggcttaactatgcggcatcagagcagattgtacTGAGAGTGCACCATAAA

ATTGTAAACGTTAATATTTTGTTAAAATTCGCGTTAAATTTTTGTTAAATCAGCTCATTTTTTAACCAATAGGCCGAA

ATCGGCAAAATCCCTTATAAATCAAAAGAATAGCCCGAGATAGGGTTGAGTGTTGTTCCAGTTTGGAACAAGAGT

CCACTATTAAAGAACGTGGACTCCAACGTCAAAG

SEQUENCE LISTING

<160> NUMBER OF SEQ ID NOS: 10

<210> SEQ ID NO 1
<211> LENGTH: 2391
<212> TYPE: DNA
<213> ORGANISM: Artificial Sequence
<220> FEATURE:
<223> OTHER INFORMATION: Synthetic Poilynucleotide

<400> SEQUENCE: 1

```
atgtcggcgg cgcaggtgtc ctcgtcccgg agacaatctt gctacctgtg cgacctgccc      60
cgcatgccct gggccatgat ctgggacttc tcggaacccg tatgccgcgg ttgcgtcaac     120
tacgagggcg ctgatcgcat cgaattcgtg atcgagacag cgcgccagct gaagcgggcg     180
cacggctgct tccaggacgg ccgctccccc gggccgccgc cgcccgtcgg ggtcaagaca     240
gtggccctgt cggctaagga agcggcggcg gcggcggcag cagcggcggc cgccgccgcc     300
gccgcgcaac agcaacagca acagcagcag cagcagcagc aacagcagca gcagcagcag     360
```

-continued

```
cagcagcagc agcaacaaca gctcaaccac gttgatggtt ccagcaagcc tgcggtgctg    420
gcggccccgt ctggcctgga gcgctacggc ctaagcgctg ccgccgccgc cgccgccgcc    480
gccgccgctg cggtggaaca gcgcagccgc ttcgagtacc cgccaccgcc ggtgagcctg    540
ggaagcagca gccacaccgc gcgactgccc aacggcctgg ggggcccaaa cggcttcccc    600
aaaccaacac cagaggaggg accccagag ctgaaccgtc agagccccaa ttcttcttca    660
gcggcggcgt cggtggcgtc tcggcgtgga acgcacggtg ggctggttac ggggctgccc    720
aacccggggg gtggcggagg cccccagctc accgtgcccc ccaacctgct accgcagacg    780
ctgcttaacg gcccggccag cgctgcggta ctcccccac ccctcccca cgccctgggc    840 agccgtgggc ccccgacgcc tgctcccca ggggctcctg ggggccccgc ttgtctcggg    900
ggtaccccgg gtgtatcggc cacgtcgtcc tccgcgtcgt cttcgacctc ttcgtcggtg    960
gcagaggtgg gcgtgggtgc tggtggtaag aggcccggct cggtgtcgag cacagaccag   1020
gagcgcgagt tgaaggagaa gcagcgcaac gccgaggccc tggccgagct gagcgagagc   1080
ctgcgcaacc gcgccgagga gtgggccagc aagcccaaga tggtccgcga cacgctgctc   1140
acgctggcag gctgcacgcc ctacgaggtt cgcttcaaga aggaccactc gctgctgggc   1200 cgcgtttcg ccttcgacgc cgtctccaag cccggcatgg actacgaatt gaagctgttc   1260
attgagtacc ccacgggctc gggcaacgtg tactccagtg catctggtgt ggccaagcag   1320
atgtatcagg actgcatgaa ggacttcggc cggggcctat cctcgggttt caagtacctg   1380
gagtacgaaa agaagcacgg ctccggggac tggcgcctgc ttggagacct gctccccgaa   1440
gccgtgcgct tcttcaagga gggcgtgccc ggcgccgaca tgctgcccca gccctacctg   1500
gacgccagct gtcccatgct gcccactgct ctggtgagtc tgagccgcgc ccccagcgca   1560
ccccggggga ccgggccctt gccgcccgcc gcgccgtcgg gccggggcgc agccgccagc   1620
ctgcgcaaga gaaaggcctc tccggagccc ccggactcag ccgagggcgc gctgaagctg   1680
ggcgaggaac agcagaggca gcagtggatg gcgaaccaga gcgaggcgct gaagctcacc   1740
atgtccgccg ggggcttcgc ggcgccgggg cacgcggcgg ggggtccgcc tccgccgccc   1800
ccacctctgg gaccccattc caaccggacc accccacctg agtcagcccc ccagaacggt   1860 ccgtcccta tggccgctct catgtcggtg gcagatactc tgggcacagc gcactcgccc   1920
aaggatggca gttccgtgca ctctaccact gcgtcggcgc ggcgaaacag cagcagccca   1980
gtctcgccgg cctccgtgcc ggggcagcgc cgcttggcat cacgtaacgg ggacctgaat   2040 ttacaggtg cgccccgcc gcctagcgcc caccgggca tggaccaagt gcacccccaa   2100
aacattccgg attccccat ggccaacagc ggacccctct gctgcaccat ttgccacgaa   2160
cgtttggagg atacgcattt cgttcagtgc ccttccgtcc ccagccacaa attttgcttc   2220
ccttgctcta gagagagtat caaggcccag ggggccaccg gcgaggtgta ttgccccagc   2280
ggagagaaat gccccctagt cgggtcgaat gtaccttggg ccttcatgca gggcgaaatc   2340
gcgactatct tagctgggga tgttaaagtg aaaaaggaga gagacccttg a           2391
```

<210> SEQ ID NO 2
<211> LENGTH: 4157
<212> TYPE: DNA
<213> ORGANISM: Artificial Sequence
<220> FEATURE:
<223> OTHER INFORMATION: Synthetic Poilynucleotide

<400> SEQUENCE: 2

-continued

```
gcgagccgca gccggagcag gagcgccgag acgcgcctcc ggaacgtaga gtaacaatca      60
caaccccaca ttccgggcga gcgtgagcac gagcgggaag ggatgcgacc cgggccgagg     120
cgccgcgcga gcgccctgca gccaacgtga gcgccgccag ccgcggcggc ccgggcgccg     180
gccaggcctg ggggcggcgg gagcctgcgt gcgtgcactc ctctcctctg ctctcgtgcg     240
tcctggaagc agtggccgcg gcggctccct ccggggtgca aacccagtcg ccgccagcag     300
aacggccgac gctgcggagg ggagaaggtc ctttctcggc tgccaccccc tccccggtc      360 ctccggggaa gcagcggctt cagcaagatt ggacccgggc accgggtggc actgaaccct     420
ctggccctcg ccccaggggg cccgtcgggg agaggacgca gctcgtaggg gggtccccgg     480
ggagaggaag agacagcccc tttcgagctt ccacgcacca gccactccgg ggaggggggcc     540 aagaggcaac ggcggccacc accgggcacc ctcgcccccct cccctcgggc cgggagcttc     600
cagcccaagt ctgcagcacc aggaagaagg cgcctgagct cccctcgcga cgagtcaacc     660
gcagtaggag gtgggggcga agagagggct gaacccgtcc gctgcccggg cggtggagcc     720
cccacggcga ggcgctgcgc cggcggtgga gactcgcgtt ccctccagcc cctggggcag     780
aactttctcg cccccccctcc tccctcccct gcagtcggac tccctcccca gccggccagt     840
cctcccggag gagaaggcgc cgcggagaca gcccgggcgg gggcctacct tccccagggc     900
aggcatcatg tcggcggcgc aggtgtcctc gtcccggaga caatcttgct acctgtgcga     960
cctgccccgc atgccctggg ccatgatctg ggacttctcg gaacccgtat gccgcggttg    1020
cgtcaactac gagggcgctg atcgcatcga attcgtgatc gagacagcgc gccagctgaa    1080
gcgggcgcac ggctgcttcc aggacggccg ctcccccggg ccgccgccgc ccgtcggggt    1140
caagacagtg gccctgtcgg ctaaggaagc ggcggcggcg gcggcagcag cggcggccgc    1200
cgccgccgcc gcgcaacagc aacagcaaca gcagcagcag cagcagcaac agcagcagca    1260
gcagcagcag cagcagcagc aacaacagct caaccacgtt gatggttcca gcaagcctgc    1320
ggtgctggcg gccccgtctg gcctggagc ctacggccta agcgctgccg ccgccgccgc    1380
cgccgccgcc gccgctgcgg tggaacagcg cagccgcttc gagtacccgc caccgccggt    1440
gagcctggga agcagcagcc acaccgcgcg actgcccaac ggcctggggg gcccaaacgg    1500
cttccccaaa ccaacaccag aggagggacc cccagagctg aaccgtcaga gccccaattc    1560
ttcttcagcg gcggcgtcgg tggcgtctcg gcgtggaacg cacggtgggc tggttacggg    1620
gctgcccaac ccggggggtg gcggaggccc ccagctcacc gtgccccca acctgctacc    1680 gcagacgctg cttaacgccc cggccagcgc tgcggtactc ccccaccccc ctccccacgc    1740
cctgggcagc cgtgggcccc cgacgcctgc tcccccaggg gctcctgggg gccccgcttg    1800
tctcgggggt accccgggtg tatcggccac gtcgtcctcc gcgtcgtctt cgacctcttc    1860
gtcggtggca gaggtgggcg tgggtgctgg tggtaagagg cccggctcgg tgtcgagcac    1920
agaccaggag cgcgagttga aggagaagca gcgcaacgcc gaggccctgg ccgagctgag    1980
cgagagcctg cgcaaccgcg ccgaggagtg ggccagcaag cccaagatgg tccgcgacac    2040
gctgctcacg ctggcaggct gcacgcccta cgaggttcgc ttcaagaagg accactcgct    2100
gctgggccgt gttttcgcct tcgacgccgt ctccaagccc ggcatggact acgaattgaa    2160
gctgttcatt gagtaccca cgggctcggg caacgtgtac tccagtgcat ctggtgtggc    2220
caagcagatg tatcaggact gcatgaagga cttcggccgg ggctatcct cgggtttcaa     2280 gtacctggag tacgaaaaga agcacggctc cggggactgg cgcctgcttg agacctgct    2340 ccccgaagcc gtgcgcttct tcaaggaggg cgtgcccggc gccgacatgc tgccccagcc    2400
```

-continued

```
ctacctggac gccagctgtc ccatgctgcc cactgctctg gtgagtctga gccgcgcccc    2460
cagcgcaccc ccggggaccg gggccttgcc gcccgccgcg ccgtcgggcc ggggcgcagc    2520
cgccagcctg cgcaagagaa aggcctctcc ggagcccccg gactcagccg agggcgcgct    2580
gaagctgggc gaggaacagc agaggcagca gtggatggcg aaccagagcg aggcgctgaa    2640
gctcaccatg tccgccgggg gcttcgcggc gccggggcac gcggcggggg gtccgcctcc    2700
gccgccccca cctctgggac cccattccaa ccggaccacc ccacctgagt cagcccccca    2760
gaacggtccg tccctatgg ccgctctcat gtcggtggca gatactctgg cacagcgca    2820 ctcgcccaag gatggcagtt ccgtgcactc taccactgcg tcggcgcggc gaaacagcag    2880
cagcccagtc tcgccggcct ccgtgccggg gcagcgccgc ttggcatcac gtaacgggga    2940
cctgaattta caggtggcgc ccccgccgcc tagcgcccac ccgggcatgg accaagtgca    3000
cccccaaaac attccggatt cccccatggc caacagcgga cccctctgct gcaccatttg    3060
ccacgaacgt ttggaggata cgcatttcgt tcagtgccct tccgtcccca gccacaaatt    3120
ttgcttccct tgctctagag agagtatcaa ggcccagggg gccaccggcg aggtgtattg    3180
ccccagcgga gagaaatgcc ccctagtcgg gtcgaatgta ccttgggcct tcatgcaggg    3240
cgaaatcgcg actatcttag ctggggatgt aaagtgaaa aaggagagag acccttgaac    3300
cactgggcag ccacctcctt tgccctagac cagctcctct ccaatcctga gggcccctcc    3360
cccaacccaa ctcgaccctc cctcccctca cccccaaggt gtagaattgt gaatataacg    3420
aaactgcaaa aagttagtct tatgtataga cattattttc gtcgtatgtt tctatatttt    3480
gaaacaaagg tatgtaactt cttcatttga aggataagct ggtttgtgtt aagcagtata    3540
gtattggttg ggtcatttgc atcatatcgt tagcatttat ttggtggcag aatgtttgcc    3600
taggtacaga attaatagcc cttagcaacg actgctgctg gtgtgtattt ttgtaaatgt    3660
tatgcactct ctgaaaggaa aaacacacac aaaagaaaaa gacttttttt tttttttttt    3720 ttttttgcc aaggccagtg ttgctgccta aaaaaaaaa aaaaaaaaa aaaaaaaaa    3780 aaaaatgcta taaatggtg aaagcttcct tctaaactgc cccaagtgtt gaagtcttca    3840
ctttattttg ttgttttgtt ttgttttct gttttgtttg caaaatggta aggggtgtc    3900 gggggggatg gggtgtattt tgttgcaagt ttgtgagggg aaaatgtttt ggtttgtttc    3960
tactgacctg aatgtgttgg atctacacgt gttgttttgt ttttgcttta ttgatgcacg    4020 gatgctttg aacagtagag cgaaatgcta gacatggaga atctgctctg tttgtccttt    4080
atacatttct gtagttaaca gaacactgta atgtgccttg gagcttagta acttgtaata    4140
aattcaattg atattaa                                                    4157
```

```
<210> SEQ ID NO 3
<211> LENGTH: 7740
<212> TYPE: DNA
<213> ORGANISM: Artificial Sequence
<220> FEATURE:
<223> OTHER INFORMATION: Synthetic Poilynucleotide

<400> SEQUENCE: 3
```

```
gggggggggg gggggggtt ggccactccc tctctgcgcg ctcgctcgct cactgaggcc     60
gggcgaccaa aggtcgcccg acgcccgggc tttgcccggg cggcctcagt gagcgagcga    120
gcgcgcagag agggagtggc caactccatc actaggggtt cctagatctg aattcggtac    180
caaaaatcga taaaaggcgc gccaaaaacg cgtgaacaac gccaggctcc tcaacaggca    240
```

-continued

```
actttgctac ttctacagaa aatgataata aagaaatgct ggtgaagtca aatgcttatc      300
acaatggtga actactcagc agggaggctc taataggcgc caagagccta gacttcctta      360
agcgccagag tccacaaggg cccagttaat cctcaacatt caaatgctgc ccacaaaacc      420 agccctctg tgccctagcc gcctcttttt tccaagtgac agtagaactc caccaatccg      480
cagctgaatg gggtccgcct ctttcctg cctaaacaga caggaactcc tgccaattga      540
gggcgtcacc gctaaggctc cgccccagcc tgggctccac aaccaatgaa gggtaatctc      600
gacaaagagc aaggggtggg gcgcgggcgc gcaggtgcag cagcacacag gctggtcggg      660
agggcggggc gcgacgtctg ccgtgcgggg tcccggcatc ggttgcgcgc gcgctccctc      720
ctctcggaga gagggctgtg gtaaaacccg tccggaaaac gcgtcgaagg gcgaattctg      780
cagataactg gtaagtttag tcttttttgt cttttatttc aggtcccgga tccgaaaagg      840
aaaggtcatc gtctgtttaa tttccacccc cagctctgga cttccagcat tagctcgccg      900
ggcctcagct gttgtacaca cacggcgagg ggggaggga gggcggaggc gcggaggagg      960
ggccggctgg gaggaatctg ggcgtcctgc cgcgcatgcg ccttgcctga gcaacaagtg     1020
ggctccacag aggaagtgta aaggggaggg ggaagaactg gtgcagagca tggcggtgac     1080
gtcagcgctc cgcccgggcg gcatcccgcg cggccaagcc ggggacagcg cgagccgcag     1140
ccggagcagg agcgccgaga cgcgcctccg gaacgtagag taacaccggt gcgagccgca     1200
gccggagcag gagcgccgag acgcgcctcc ggaacgtaga gtaacaatca caaccccaca     1260
ttccgggcga gcgtgagcac gagcgggaag ggatgcgacc cgggccgagg cgccgcgcga     1320
gcgccctgca gccaacgtga gcgccgccag ccgcggcggc ccgggcgccg gccaggcctg     1380
ggggcggcgg gagcctgcgt gcgtgcactc ctctcctctg ctctcgtgcg tcctggaagc     1440
agtggccgcg gcggctccct ccggggtgca aacccagtcg ccgccagcag aacggccgac     1500
gctgcggagg ggagaaggtc ctttctcggc tgccacccc tcccccggtc ctccggggaa     1560
gcagcggctt cagcaagatt ggacccgggc accgggtggc actgaacct ctggccctcg     1620 ccccagggg cccgtcgggg agaggacgca gctcgtaggg gggtccccgg ggagaggaag     1680
agacagcccc tttcgagctt ccacgcacca gccactccgg ggagggggcc aagaggcaac     1740
ggcggccacc accgggcacc ctcgccccct ccctcgggc cgggagcttc cagcccaagt     1800
ctgcagcacc aggaagaagg cgcctgagct ccctcgcga cgagtcaacc gcagtaggag     1860 gtggggcga agagagggct gaacccgtcc gctgcccggg cggtggagcc cccacggcga     1920
ggcgctgcgc cggcggtgga gactcgcgtt ccctccagcc cctggggcag aactttctcg     1980 cccccctcc tccctccccc gcagtcggac tccctcccca gccggccagt cctcccggag     2040
gagaaggcgc cgcggagaca gcccgggcgg gggcctacct tccccagggc aggcatcatg     2100
tcggcggcgc aggtgtcctc gtcccggaga caatcttgct acctgtgcga cctgccccgc     2160
atgccctggg ccatgatctg ggacttctcg gaacccgtat gccgcggttg cgtcaactac     2220
gagggcgctg atcgcatcga attcgtgatc gagacagcgc gccagctgaa gcgggcgcac     2280
ggctgcttcc aggacggccg ctcccccggg ccgccgccgc ccgtcggggt caagacagtg     2340
gccctgtcgg ctaaggaagc ggcgcgcgcg gcggcagcag cggcggccgc cgccgccgcc     2400
gcgcaacagc aacagcaaca gcagcagcag cagcagcaac agcagcagca gcagcagcag     2460
cagcagcagc aacaacagct caaccacgtt gatggttcca gcaagcctgc ggtgctggcg     2520
gccccgtctg gcctggagcg ctacggccta agcgctgccg ccgccgccgc cgccgccgcc     2580
gccgctgcgg tggaacagcg cagccgcttc gagtacccgc caccgccggt gagcctggga     2640
```

-continued

```
agcagcagcc acaccgcgcg actgcccaac ggcctggggg gcccaaacgg cttccccaaa    2700
ccaacaccag aggagggacc cccagagctg aaccgtcaga gccccaattc ttcttcagcg    2760
gcggcgtcgg tggcgtctcg gcgtggaacg cacggtgggc tggttacggg gctgcccaac    2820
ccggggggtg gcggaggccc ccagctcacc gtgccccca acctgctacc gcagacgctg    2880
cttaacggcc cggccagcgc tgcggtactc ccccacccc ctccccacgc cctgggcagc    2940
cgtgggcccc cgacgcctgc tcccccaggg gctcctgggg gccccgcttg tctcgggggt    3000
accccgggtg tatcggccac gtcgtcctcc gcgtcgtctt cgacctcttc gtcggtggca    3060
gaggtgggcg tgggtgctgg tggtaagagg cccggctcgg tgtcgagcac agaccaggag    3120
cgcgagttga aggagaagca gcgcaacgcc gaggccctgg ccgagctgag cgagagcctg    3180
cgcaaccgcg ccgaggagtg ggccagcaag cccaagatgg tccgcgacac gctgctcacg    3240
ctggcaggct gcacgcccta cgaggttcgc ttcaagaagg accactcgct gctgggccgc    3300
gttttcgcct tcgacgccgt ctccaagccc ggcatggact acgaattgaa gctgttcatt    3360
gagtacccca cgggctcggg caacgtgtac tccagtgcat ctggtgtggc caagcagatg    3420
tatcaggact gcatgaagga cttcggccgg ggcctatcct cgggtttcaa gtacctggag    3480
tacgaaaaga agcacggctc cggggactgg cgcctgcttg gagacctgct ccccgaagcc    3540
gtgcgcttct tcaaggaggg cgtgcccggc gccgacatgc tgccccagcc ctacctggac    3600
gccagctgtc ccatgctgcc cactgctctg gtgagtctga gccgcgcccc cagcgcaccc    3660
ccggggaccg gggccttgcc gcccgccgcg ccgtcgggcc ggggcgcagc cgccagcctg    3720
cgcaagagaa aggcctctcc ggagcccccg gactcagccg agggcgcgct gaagctgggc    3780
gaggaacagc agaggcagca gtggatggcg aaccagagcg aggcgctgaa gctcaccatg    3840
tccgccgggg gcttcgcggc gccggggcac gcggcggggg gtccgcctcc gccgcccca    3900 cctctgggac cccattccaa ccggaccacc ccacctgagt cagcccccca gaacggtccg    3960
tcccctatgg ccgctctcat gtcggtggca gatactctgg gcacagcgca ctcgcccaag    4020
gatggcagtt ccgtgcactc taccactgcg tcggcgcggc gaaacagcag cagcccagtc    4080
tcgccggcct ccgtgccggg gcagcgccgc ttggcatcac gtaacgggga cctgaattta    4140
caggtggcgc ccccgccgcc tagcgcccac ccgggcatgg accaagtgca cccccaaaac    4200
attccggatt cccccatggc caacagcgga cccctctgct gcaccatttg ccacgaacgt    4260
ttggaggata cgcatttcgt tcagtgccct tccgtcccca gccacaaatt ttgcttccct    4320
tgctctagag agagtatcaa ggcccagggg gccaccggcg aggtgtattg ccccagcgga    4380
gagaaatgcc ccctagtcgg gtcgaatgta ccttgggcct tcatgcaggg cgaaatcgcg    4440
actatcttag ctggggatgt aaaagtgaaa aaggagagag acccttgaaa gcttaataaa    4500
agatctttat tttcattaga tctgtgtgtt ggttttttgt gtgaaactcg agaagatatc    4560
aactgccttc tactgggcgg ttttatggac agcaagcgaa ccggaattgc cagctggggc    4620
gccctctggt aaggttggga agccctgcaa agtaaactgg atggctttct cgccgccaag    4680
gatctgatgg cgcaggggat caagctctga tcaagagaca ggatgaggat cgtttcgcgt    4740
tcttgactct tcgcgatgta cgggccagat atacgcgttg acattgatta ttgactagtt    4800
attaatagta atcaattacg gggtcattag ttcatagccc atatatggag ttccgctcga    4860
gcaaaggcgc gccaaaaaag catgctgggg agagatctag gaacccctag tgatggagtt    4920
ggccactccc tctctgcgcg ctcgctcgct cactgaggcc gcccgggcaa agcccgggcg    4980
```

-continued

```
tcgggcgacc tttggtcgcc cggcctcagt gagcgagcga gcgcgcagag agggagtggc      5040
caaccccccc cccccccccc ctgcagccct gcattaatga atcggccaac gcgcggggag      5100
aggcggtttg cgtattgggc gctcttccgc ttcctcgctc actgactcgc tgcgctcggt      5160
cgttcggctg cggcgagcgg tatcagctca ctcaaaggcg gtaatacggt tatccacaga      5220
atcaggggat aacgcaggaa agaacatgtg agcaaaaggc cagcaaaagg ccaggaaccg      5280
taaaaaggcc gcgttgctgg cgtttttcca taggctccgc cccctgacg agcatcacaa       5340 aaatcgacgc tcaagtcaga ggtggcgaaa cccgacagga ctataaagat accaggcgtt      5400
tcccctggaa gctccctcg tgcgctctcc tgttccgacc ctgccgctta ccggatacct       5460
gtccgccttt ctcccttcgg gaagcgtggc gctttctcaa tgctcacgct gtaggtatct      5520
cagttcggtg taggtcgttc gctccaagct gggctgtgtg cacgaacccc ccgttcagcc      5580
cgaccgctgc gccttatccg gtaactatcg tcttgagtcc aacccggtaa gacacgactt      5640
atcgccactg gcagcagcca ctggtaacag gattagcaga gcgaggtatg taggcggtgc      5700
tacagagttc ttgaagtggt ggcctaacta cggctacact agaaggacag tatttggtat      5760
ctgcgctctg ctgaagccag ttaccttcgg aaaaagagtt ggtagctctt gatccggcaa      5820
acaaaccacc gctggtagcg gtggtttttt tgtttgcaag cagcagatta cgcgcagaaa      5880
aaaaggatct caagaagatc ctttgatctt ttctacgggg tctgacgctc agtggaacga      5940
aaactcacgt taagggattt tggtcatgag acaataaccc tgataaatgc ttcaataata      6000
ttgaaaaagg aagagtatga gccatattca acgggaaacg tcgaggccgc gattaaattc      6060
caacatggat gctgatttat atgggtataa atgggctcgc gataatgtcg ggcaatcagg      6120
tgcgacaatc tatcgcttgt atgggaagcc cgatgcgcca gagttgtttc tgaaacatgg      6180
caaaggtagc gttgccaatg atgttacaga tgagatggtc agactaaact ggctgacgga      6240
atttatgcca cttccgacca tcaagcattt tatccgtact cctgatgatg catggttact      6300
caccactgcg atccccggaa aaacagcgtt ccaggtatta gaagaatatc ctgattcagg      6360
tgaaaatatt gttgatgcgc tggcagtgtt cctgcgccgg ttgcactcga ttcctgtttg      6420
taattgtcct tttaacagcg atcgcgtatt tcgcctcgct caggcgcaat cacgaatgaa      6480
taacggtttg gttgatgcga gtgattttga tgacgagcgt aatggctggc ctgttgaaca      6540
agtctggaaa gaaatgcata aacttttgcc attctcaccg gattcagtcg tcactcatgg      6600
tgatttctca cttgataacc ttattttttga cgaggggaaa ttaataggtt gtattgatgt      6660
tggacgagtc ggaatcgcag accgatacca ggatcttgcc atcctatgga actgcctcgg      6720
tgagttttct ccttcattac agaaacggct ttttcaaaaa tatggtattg ataatcctga      6780
tatgaataaa ttgcagtttc atttgatgct cgatgagttt ttctaactgt cagaccaagt      6840
ttactcatat atactttaga ttgatttaaa acttcatttt taatttaaaa ggatctaggt      6900
gaagatcctt tttgataatc tcatgacatt aacctataaa aataggcgta tcacgaggcc      6960
ctttcgtctc gcgcgtttcg gtgatgacgg tgaaaacctc tgacacatgc agctcccgga      7020
gacggtcaca gcttgtctgt aagcggatgc cgggagcaga caagcccgtc agggcgcgtc      7080
agcgggtgtt ggcgggtgtc ggggctggct taactatgcg gcatcagagc agattgtact      7140
gagagtgcac catatgcggt gtgaaatacc gcacagatgc gtaaggagaa aataccgcat      7200
caggaaattg taaacgttaa tattttgtta aaattcgcgt taaatttttg ttaaatcagc      7260 tcattttttta accaataggc cgaaatcggc aaaatccctt ataaatcaaa agaatagacc      7320
gagatagggt tgagtgttgt tccagtttgg aacaagagtc cactattaaa gaacgtggac      7380
```

-continued

```
tccaacgtca aagggcgaaa aaccgtctat cagggcgatg gcccactacg tgaaccatca      7440
ccctaatcaa gttttttggg gtcgaggtgc cgtaaagcac taaatcggaa ccctaaaggg      7500
agcccccgat ttagagcttg acggggaaag ccggcgaacg tggcgagaaa ggaagggaag      7560
aaagcgaaag gagcgggcgc tagggcgctg gcaagtgtag cggtcacgct gcgcgtaacc      7620
accacacccg ccgcgcttaa tgcgccgcta cagggcgcgt cgcgccattc gccattcagg      7680
ctacgcaact gttgggaagg gcgatcggtg cgggcctctt cgctattacg ccaggctgca      7740
```

```
<210> SEQ ID NO 4
<211> LENGTH: 7385
<212> TYPE: DNA
<213> ORGANISM: Artificial Sequence
<220> FEATURE:
<223> OTHER INFORMATION: Synthetic Poilynucleotide

<400> SEQUENCE: 4
```

```
gggggggggg ggggggggtt ggccactccc tctctgcgcg ctcgctcgct cactgaggcc        60
gggcgaccaa aggtcgcccg acgcccgggc tttgcccggg cggcctcagt gagcgagcga       120
gcgcgcagag agggagtggc caactccatc actaggggtt cctagatctg aattcggtac       180
cggttcctag atcagggcac aaaaacaaat agaaaagaca atttctggaa gattggaaaa       240
cagctaattt tgcaggtgct tcggcatcag tggtggcgat gaatttaaca tccatgccgg       300
gggggataag gttcaaccgc agatgaaatg gttaatacct tatacgaaat tcacggcgaa       360
aaatcctgaa acaggacatt taaattcact gccgaggctt gggggtgggg tggggagcag       420
ggatcggaaa cgacgctagt ggttcttaaa tgcgttttta cttgggaatg cccggcaggg       480
aaaggaaagg tcatcgtctg tttaatttcc accccagct ctggacttcc agcattagct       540
cgccgggcct cagctgttgt acacacacgg cgaggggggga ggggagggcg gaggcgcgga       600 ggagggggccg gctgggagga atctgggcgt cctgccgcgc atgcgccttg cctgagcaac       660
aagtgggctc cacagaggaa gtgtaaaggg gaggggggaag aactggtgca gagcatggcg       720
gtgacgtcag cgctccgccc gggcggcatc ccgcgcggcc aagccgggga cagcgcgagc       780
cgcagccgga gcaggagcgc cgagacgcgc ctccggaacg tagagtaacg gatccgcgag       840
ccgcagccgg agcaggagcg ccgagacgcc cctccggaac gtagagtaac aatcacaacc       900
ccacattccg ggcgagcgtg agcacgagcg ggaaggggatg cgacccgggc cgaggcgccg       960
cgcgagcgcc ctgcagccaa cgtgagcgcc gccagccgcg gcggcccggg cgccggccag      1020 gcctggggggc ggcgggagcc tgcgtgcgtg cactcctctc ctctgctctc gtgcgtcctg      1080
gaagcagtgg ccgcggcggc tccctccggg gtgcaaaccc agtcgccgcc agcagaacgg      1140
ccgacgctgc ggagggggaga aggtcctttc tcggctgcca ccccctcccc cggtcctccg      1200
gggaagcagc ggcttcagca agattggacc cgggcaccgg gtggcactga accctctggc      1260
cctcgcccca gggggcccgt cggggagagg acgcagctcg tagggggggtc cccgggggaga      1320 ggaagagaca gcccctttcg agcttccacg caccagccac tccggggagg gggccaagag      1380
gcaacggcgg ccaccaccgg gcaccctcgc ccctcccct cgggccggga gcttccagcc      1440
caagtctgca gcaccaggaa gaaggcgcct gagctccct cgccgacgagt caaccgcagt      1500 aggaggtggg ggcgaagaga gggctgaacc cgtccgctgc ccggggcggtg gagcccccac      1560 ggcgaggcgc tgcgccggcg gtggagactc gcgttccctc cagccctgg ggcagaactt      1620 tctcgcccccc cctcctccct ccccgcagt cggactccct ccccagccgg ccagtcctcc      1680
```

```
cggaggagaa ggcgccgcgg agacagcccg ggcggggggcc taccttcccc agggcaggca      1740
tcatgtcggc ggcgcaggtg tcctcgtccc ggagacaatc ttgctacctg tgcgacctgc      1800
cccgcatgcc ctgggccatg atctgggact tctcggaacc cgtatgccgc ggttgcgtca      1860
actacgaggg cgctgatcgc atcgaattcg tgatcgagac agcgcgccag ctgaagcggg      1920
cgcacggctg cttccaggac ggccgctccc ccgggccgcc gccgcccgtc ggggtcaaga      1980
cagtggccct gtcggctaag gaagcggcgg cggcggcggc agcagcggcg gccgccgccg      2040
ccgccgcgca acagcaacag caacagcagc agcagcagca gcaacagcag cagcagcagc      2100
agcagcagca gcagcaacaa cagctcaacc acgttgatgg ttccagcaag cctgcggtgc      2160
tggcggcccc gtctggcctg gagcgctacg gcctaagcgc tgccgccgcc gccgccgccg      2220
ccgccgccgc tgcggtggaa cagcgcagcc gcttcgagta cccgccaccg ccggtgagcc      2280
tgggaagcag cagccacacc gcgcgactgc ccaacggcct gggggggccca aacggcttcc      2340 ccaaaccaac accagaggag ggacccccag agctgaaccg tcagagcccc aattcttctt      2400
cagcggcggc gtcggtggcg tctcggcgtg gaacgcacg tgggctggtt acggggctgc      2460
ccaacccggg gggtggcgga ggccccccagc tcaccgtgcc ccccaacctg ctaccgcaga      2520
cgctgcttaa cggcccggcc agcgctgcgg tactccccc accccctccc cacgccctgg      2580
gcagccgtgg gccccccgacg cctgctcccc caggggctcc tgggggcccc gcttgtctcg      2640
ggggtacccc gggtgtatcg gccacgtcgt cctccgcgtc gtcttcgacc tcttcgtcgg      2700
tggcagaggt gggcgtgggt gctggtggta agaggcccgg ctcggtgtcg agcacagacc      2760
aggagcgcga gttgaaggag aagcagcgca acgccgaggc cctggccgag ctgagcgaga      2820
gcctgcgcaa ccgcgccgag gagtgggcca gcaagcccaa gatggtccgc gacacgctgc      2880
tcacgctggc aggctgcacg ccctacgagg ttcgcttcaa gaaggaccac tcgctgctgg      2940
gccgcgtttt cgccttcgac gccgtctcca gcccggcat ggactacgaa ttgaagctgt      3000
tcattgagta ccccacgggc tcgggcaacg tgtactccag tgcatctggt gtggccaagc      3060
agatgtatca ggactgcatg aaggacttcg gccggggcct atcctcgggt ttcaagtacc      3120
tggagtacga aaagaagcac ggctccgggg actggcgcct gcttggagac ctgctccccg      3180
aagccgtgcg cttcttcaag gagggcgtgc ccggcgccga catgctgccc cagccctacc      3240
tggacgccag ctgtcccatg ctgcccactg ctctggtgag tctgagccgc gcccccagcg      3300
cacccccggg gaccgggggcc ttgccgcccg ccgcgccgtc gggccggggc gcagccgcca      3360
gcctgcgcaa gagaaaggcc tctccggagc ccccggactc agccgagggc gcgctgaagc      3420
tgggcgagga acagcagagg cagcagtgga tggcgaacca gagcgaggcg ctgaagctca      3480
ccatgtccgc cggggggcttc gcggcgccgg ggcacgcggc ggggggtccg cctccgccgc      3540
ccccacctct gggaccccat tccaaccgga ccacccacc tgagtcagcc ccccagaacg      3600
gtccgtcccc tatggccgct ctcatgtcgg tggcagatac tctgggcaca gcgcactcgc      3660
ccaaggatgg cagttccgtg cactctacca ctgcgtcggc gcggcgaaac agcagcagcc      3720
cagtctcgcc ggcctccgtg ccggggcagc gccgcttggc atcacgtaac ggggacctga      3780
atttacaggt ggcgcccccg ccgcctagcc cccaccccggg catggaccaa gtgcacccc      3840 aaaacattcc ggattccccc atggccaaca gcggacccct ctgctgcacc atttgccacg      3900
aacgtttgga ggatacgcat ttcgttcagt gcccttccgt ccccagccac aaattttgct      3960
tcccttgctc tagagagagt atcaaggccc aggggggccac cggcgaggtg tattgcccca      4020
gcggagagaa atgcccccta gtcgggtcga atgtaccttg ggccttcatg cagggcgaaa      4080
```

-continued

```
tcgcgactat cttagctggg gatgttaaag tgaaaaagga gagagaccct tgaaagctta   4140
ataaaagatc tttattttca ttagatctgt gtgttggttt tttgtgtgaa actcgagaag   4200
atatcaactg ccttctactg ggcggtttta tggacagcaa gcgaaccgga attgccagct   4260
ggggcgccct ctggtaaggt tgggaagccc tgcaaagtaa actggatggc tttctcgccg   4320
ccaaggatct gatggcgcag gggatcaagc tctgatcaag agacaggatg aggatcgttt   4380
cgcgttcttg actcttcgcg atgtacgggc cagatatacg cgttgacatt gattattgac   4440
tagttattaa tagtaatcaa ttacggggtc attagttcat agcccatata tggagttccg   4500
ctcgagcaaa ggcgcgccaa aaaagcatgc tggggagaga tctaggaacc cctagtgatg   4560
gagttggcca ctccctctct gcgcgctcgc tcgctcactg aggccgcccg ggcaaagccc   4620
gggcgtcggg cgacctttgg tcgcccggcc tcagtgagcg agcgagcgcg cagagaggga   4680
gtggccaacc cccccccccc ccccctgca gccctgcatt aatgaatcgg ccaacgcgcg   4740
gggagaggcg gtttgcgtat tgggcgctct tccgcttcct cgctcactga ctcgctgcgc   4800
tcggtcgttc ggctgcggcg agcggtatca gctcactcaa aggcggtaat acggttatcc   4860
acagaatcag gggataacgc aggaaagaac atgtgagcaa aaggccagca aaaggccagg   4920
aaccgtaaaa aggccgcgtt gctggcgttt ttccataggc tccgcccccc tgacgagcat   4980
cacaaaaatc gacgctcaag tcagaggtgg cgaaacccga caggactata aagataccag   5040
gcgtttcccc ctggaagctc cctcgtgcgc tctcctgttc cgaccctgcc gcttaccgga   5100
tacctgtccg cctttctccc ttcgggaagc gtggcgcttt ctcaatgctc acgctgtagg   5160
tatctcagtt cggtgtaggt cgttcgctcc aagctgggct gtgtgcacga accccccgtt   5220
cagcccgacc gctgcgcctt atccggtaac tatcgtcttg agtccaaccc ggtaagacac   5280
gacttatcgc cactggcagc agccactggt aacaggatta gcagagcgag gtatgtaggc   5340
ggtgctacag agttcttgaa gtggtggcct aactacggct acactagaag gacagtattt   5400
ggtatctgcg ctctgctgaa gccagttacc ttcggaaaaa gagttggtag ctcttgatcc   5460
ggcaaacaaa ccaccgctgg tagcggtggt ttttttgttt gcaagcagca gattacgcgc   5520
agaaaaaaag gatctcaaga agatcctttg atcttttcta cggggtctga cgctcagtgg   5580
aacgaaaact cacgttaagg gattttggtc atgagacaat aaccctgata aatgcttcaa   5640
taatattgaa aaaggaagag tatgagccat attcaacggg aaacgtcgag gccgcgatta   5700
aattccaaca tggatgctga tttatatggg tataaatggg ctcgcgataa tgtcgggcaa   5760
tcaggtgcga caatctatcg cttgtatggg aagcccgatg cgccagagtt gtttctgaaa   5820
catggcaaag gtagcgttgc caatgatgtt acagatgaga tggtcagact aaactggctg   5880
acggaattta tgccacttcc gaccatcaag cattttatcc gtactcctga tgatgcatgg   5940
ttactcacca ctgcgatccc cggaaaaaca gcgttccagg tattagaaga atatcctgat   6000
tcaggtgaaa atattgttga tgcgctggca gtgttcctgc gccggttgca ctcgattcct   6060
gtttgtaatt gtccttttaa cagcgatcgc gtatttcgcc tcgctcaggc gcaatcacga   6120
atgaataacg gtttggttga tgcgagtgat tttgatgacg agcgtaatgg ctggcctgtt   6180
gaacaagtct ggaaagaaat gcataaactt ttgccattct caccggattc agtcgtcact   6240
catggtgatt tctcacttga taaccttatt tttgacgagg ggaaattaat aggttgtatt   6300
gatgttggac gagtcggaat cgcagaccga taccaggatc ttgccatcct atggaactgc   6360
ctcggtgagt tttctccttc attacagaaa cggctttttc aaaaatatgg tattgataat   6420
```

-continued

```
cctgatatga ataaattgca gtttcatttg atgctcgatg agttttttcta actgtcagac      6480 caagtttact catatatact ttagattgat ttaaaacttc atttttaatt taaaaggatc      6540
taggtgaaga tccttttttga taatctcatg acattaacct ataaaaatag gcgtatcacg      6600 aggcccttttc gtctcgcgcg tttcggtgat gacggtgaaa acctctgaca catgcagctc      6660
ccggagacgg tcacagcttg tctgtaagcg gatgccggga gcagacaagc ccgtcagggc      6720
gcgtcagcgg gtgttggcgg gtgtcggggc tggcttaact atgcggcatc agagcagatt      6780
gtactgagag tgcaccatat gcggtgtgaa ataccgcaca gatgcgtaag gagaaaatac      6840
cgcatcagga aattgtaaac gttaatattt tgttaaaatt cgcgttaaat ttttgttaaa      6900
tcagctcatt ttttaaccaa taggccgaaa tcggcaaaat cccttataaa tcaaaagaat      6960
agaccgagat agggttgagt gttgttccag tttggaacaa gagtccacta ttaaagaacg      7020
tggactccaa cgtcaaaggg cgaaaaaccg tctatcaggg cgatggccca ctacgtgaac      7080
catcacccta atcaagtttt ttggggtcga ggtgccgtaa agcactaaat cggaaccct      7140 aagggagccc ccgatttaga gcttgacggg gaaagccggc gaacgtggcg agaaaggaag      7200
ggaagaaagc gaaaggagcg ggcgctaggg cgctggcaag tgtagcggtc acgctgcgcg      7260
taaccaccac acccgccgcg cttaatgcgc cgctacaggg cgcgtcgcgc cattcgccat      7320
tcaggctacg caactgttgg gaagggcgat cggtgcgggc ctcttcgcta ttacgccagg      7380
ctgca                                                                  7385
```

```
<210> SEQ ID NO 5
<211> LENGTH: 546
<212> TYPE: DNA
<213> ORGANISM: Artificial Sequence
<220> FEATURE:
<223> OTHER INFORMATION: Synthetic Poilynucleotide
<220> FEATURE:
<221> NAME/KEY: misc_feature
<223> OTHER INFORMATION: P546 promoter

<400> SEQUENCE: 5
gaacaacgcc aggctcctca acaggcaact ttgctacttc tacagaaaat gataataaag       60
aaatgctggt gaagtcaaat gcttatcaca atggtgaact actcagcagg gaggctctaa      120
taggcgccaa gagcctagac ttccttaagc gccagagtcc acaagggccc agttaatcct      180
caacattcaa atgctgccca caaaaccagc ccctctgtgc cctagccgcc tcttttttcc      240
aagtgacagt agaactccac caatccgcag ctgaatgggg tccgcctctt ttccctgcct      300
aaacagacag gaactcctgc caattgaggg cgtcaccgct aaggctccgc cccagcctgg      360
gctccacaac caatgaaggg taatctcgac aaagagcaag gggtggggcg cgggcgcgca      420
ggtgcagcag cacacaggct ggtcgggagg cgggggcgcg acgtctgccg tgcggggtcc      480
cggcatcggt tgcgcgcgcg ctccctcctc tcggagagag ggctgtggta aaacccgtcc      540
ggaaaa                                                                 546
```

```
<210> SEQ ID NO 6
<211> LENGTH: 270
<212> TYPE: DNA
<213> ORGANISM: Artificial Sequence
<220> FEATURE:
<223> OTHER INFORMATION: Synthetic Poilynucleotide
<220> FEATURE:
<221> NAME/KEY: misc_feature
<223> OTHER INFORMATION: hybrid chicken B -Actin promoter

<400> SEQUENCE: 6
```

-continued

```
ccacgttctg cttcactctc cccatctccc ccccctcccc accccccaatt ttgtatttat      60 ttatttttta attattttgt gcagcgatgg gggcggggggg gggggggggg cgcgcgccag     120
gcggggcggg gcggggcgag gggcgggggcg gggcgaggcg gagaggtgcg gcggcagcca     180
atcagagcgg cgcgctccga aagtttcctt ttatggcgag gcggcggcgg cggcggccct     240
ataaaaagcg aagcgcgcgg cgggcgggag                                       270
```

<210> SEQ ID NO 7
<211> LENGTH: 7170
<212> TYPE: DNA
<213> ORGANISM: Artificial Sequence
<220> FEATURE:
<223> OTHER INFORMATION: Synthetic Polynucleotide

<400> SEQUENCE: 7

```
ggcgaaaaac cgtctatcag ggcgatggcc cactacgtga accatcaccc aaatcaagtt      60 ttttgggggtc gaggtgccgt aaagcactaa atcggaaccc taaagggagc ccccgatttta    120 gagcttgacg gggaaagccg gcgaacgtgg cgagaaagga agggaagaaa gcgaaaggag     180
cgggcgctag ggcgctggca agtgtagcgg tcacgctgcg cgtaaccacc acacccgccg     240
cgcttaatgc gccgctacag ggcgcgtact atggttgctt tgacgtatgc ggtgtgaaat     300
accgcacaga tgcgtaagga gaaaataccg catcaggcgc ccctgcaggc agctgcgcgc     360
tcgctcgctc actgaggccg cccgggcaaa gcccgggcgt cgggcgacct ttggtcgccc     420
ggcctcagtg agcgagcgag cgcgcagaga gggagtggcc aactccatca ctaggggttc     480
ctgcggcgcg gccgcggtac caaaaatcga taaaaggcgc gccaaaaacg cgtgaacaac     540
gccaggctcc tcaacaggca actttgctac ttctacagaa aatgataata aagaaatgct     600
ggtgaagtca aatgcttatc acaatggtga actactcagc agggaggctc taataggcgc     660
caagagccta gacttcctta agcgccagag tccacaaggg cccagttaat cctcaacatt     720
caaatgctgc ccacaaaacc agcccctctg tgccctagcc gcctcttttt tccaagtgac     780
agtagaactc caccaatccg cagctgaatg gggtccgcct cttttccctg cctaaacaga     840
caggaactcc tgccaattga gggcgtcacc gctaaggctc cgcccagcc tgggctccac      900 aaccaatgaa gggtaatctc gacaaagagc aaggggtggg gcgcgggcgc gcaggtgcag     960
cagcacacag gctggtcggg agggcggggc gcgacgtctg ccgtgcgggg tcccggcatc    1020
ggttgcgcgc gcgctccctc ctctcggaga gagggctgtg gtaaaacccg tccggaaaac    1080
gcgtcgaagg gcgaattctg cagataactg gtaagtttag tctttttgt cttttatttc     1140 aggtcccgga tccggtggtg gtgcaaatca aagaactgct cctcagtcga tgttgccttt    1200
acttctaggc ctgtacggaa accggtgcga gccgcagccg gagcaggagc gccgagacgc    1260
gcctccggaa cgtagagtaa caatcacaac cccacattcc gggcgagcgt gagcacgagc    1320
gggaagggat gcgacccggg ccgaggcgcc gcgcgagcgc cctgcagcca acgtgagcgc    1380
cgccagccgc ggcggcccgg gcgccggcca ggcctggggg cggcgggagc ctgcgtgcgt    1440
gcactcctct cctctgctct cgtgcgtcct ggaagcagtg gccgcggcgg ctccctccgg    1500
ggtgcaaacc cagtcgccgc cagcagaacg gccgacgctg cggaggggag aaggtccttt    1560
ctcggctgcc acccctcccc ccggtcctcc ggggaagcag cggcttcagc aagattggac    1620
ccgggcaccg ggtggcactg aaccctctgg ccctcgcccc aggggccccg tcggggagag    1680
gacgcagctc gtaggggggt ccccggggag aggaagagac agcccctttc gagcttccac    1740
```

-continued

```
gcaccagcca ctccggggag ggggccaaga ggcaacggcg gccaccaccg ggcaccctcg    1800 cccccctcccc tcgggccggg agcttccagc ccaagtctgc agcaccagga agaaggcgcc   1860
tgagctcccc tcgcgacgag tcaaccgcag taggaggtgg gggcgaagag agggctgaac   1920
ccgtccgctg cccgggcggt ggagccccca cggcgaggcg ctgcgccggc ggtggagact    1980
cgcgttccct ccagcccctg gggcagaact ttctcgcccc ccctcctccc tcccccgcag    2040
tcggactccc tccccagccg gccagtcctc ccggaggaga aggcgccgcg gagacagccc    2100 gggcggggggc ctaccttccc cagggcaggc atcatgtcgg cggcgcaggt gtcctcgtcc    2160
cggagacaat cttgctacct gtgcgacctg ccccgcatgc cctgggccat gatctgggac    2220
ttctcggaac ccgtatgccg cggttgcgtc aactacgagg gcgctgatcg catcgaattc    2280
gtgatcgaga cagcgcgcca gctgaagcgg gcgcacggct gcttccagga cggccgctcc    2340
cccgggccgc cgccgcccgt cggggtcaag acagtggccc tgtcggctaa ggaagcggcg    2400
gcggcggcgg cagcagcggc ggccgccgcc gccgccgcgc aacagcaaca gcaacagcag    2460
cagcagcagc agcaacagca gcagcagcag cagcagcagc agcagcaaca acagctcaac    2520
cacgttgatg gttccagcaa gcctgcggtg ctggcggccc cgtctggcct ggagcgctac    2580
ggcctaagcg ctgccgccgc cgccgccgcc gccgccgccg ctgcggtgga acagcgcagc    2640
cgcttcgagt acccgccacc gccggtgagc ctgggaagca gcagccacac cgcgcgactg    2700
cccaacggcc tggggggccc aaacggcttc cccaaaccaa caccagagga gggaccccca    2760
gagctgaacc gtcagagccc caattcttct tcagcggcgg cgtcggtggc gtctcggcgt    2820
ggaacgcacg gtgggctggt tacggggctg cccaacccgg ggggtggcgg aggcccccag    2880
ctcaccgtgc cccccaacct gctaccgcag acgctgctta acggcccggc cagcgctgcg    2940
gtactccccc caccccctcc ccacgccctg ggcagccgtg ggcccccgac gcctgctccc    3000
ccaggggctc ctggggggccc cgcttgtctc gggggtaccc cgggtgtatc ggccacgtcg    3060
tcctccgcgt cgtcttcgac ctcttcgtcg gtggcagagg tgggcgtggg tgctggtggt    3120
aagaggcccg gctcggtgtc gagcacagac caggagcgcg agttgaagga gaagcagcgc    3180
aacgccgagg ccctggccga gctgagcgag agcctgcgca accgcgccga ggagtgggcc    3240
agcaagccca agatggtccg cgacacgctg ctcacgctgg caggctgcac gccctacgag    3300
gttcgcttca agaaggacca ctcgctgctg ggccgcgttt tcgccttcga cgccgtctcc    3360
aagcccggca tggactacga attgaagctg ttcattgagt accccacggg ctcgggcaac    3420
gtgtactcca gtgcatctgg tgtggccaag cagatgtatc aggactgcat gaaggacttc    3480 ggccgggggcc tatcctcggg tttcaagtac ctggagtacg aaaagaagca cggctccggg    3540
gactggcgcg tgcttggaga cctgctcccc gaagccgtgc gcttcttcaa ggagggcgtg    3600
cccggcgccg acatgctgcc ccagccctac ctggacgcca gctgtcccat gctgcccact    3660
gctctggtga gtctgagccg cgcccccagc gcaccccggg gaccggggc cttgccgccc    3720 gccgcgccgt cgggccgggg cgcagccgcc agcctgcgca agagaaaggc ctctccggag    3780
cccccggact cagccgaggg cgcgctgaag ctgggcgagg aacagcagag gcagcagtgg    3840
atggcgaacc agagcgaggc gctgaagctc accatgtccg ccgggggcttt cgcggcgccc    3900 gggcacgcgg cgggggggtcc gcctccgccg ccccacctc tgggaccccca ttccaaccgg    3960 accaccccac ctgagtcagc cccccagaac ggtccgtccc ctatggccgc tctcatgtcg    4020
gtggcagata tctctgggcac agcgcactcg cccaaggatg gcagttccgt gcactctacc    4080
actgcgtcgg cgcggcgaaa cagcagcagc ccagtctcgc cggcctccgt gccggggcag    4140
```

-continued

```
cgccgcttgg catcacgtaa cggggacctg aatttacagg tggcgccccc gccgcctagc      4200
gcccacccgg gcatggacca agtgcacccc caaaacattc cggattcccc catggccaac      4260
agcggacccc tctgctgcac catttgccac gaacgtttgg aggatacgca tttcgttcag      4320
tgcccttccg tccccagcca caaattttgc ttcccttgct ctagagagag tatcaaggcc      4380 caggggggcca ccggcgaggt gtattgcccc agcggagaga aatgcccccct agtcgggtcg      4440 aatgtacctt gggccttcat gcagggcgaa atcgcgacta tcttagctgg ggatgttaaa      4500
gtgaaaaagg agagagaccc ttgaaagctt aataaaagat ctttattttc attagatctg      4560
tgtgttggtt ttttgtgtga aactcgagaa gatatcaact gccttctact gggcggtttt      4620
atggacagca agcgaaccgg aattgccagc tggggcgccc tctggtaagg ttgggaagcc      4680
ctgcaaagta aactggatgg cttttctcgcc gccaaggatc tgatggcgca ggggatcaag      4740
ctctgatcaa gagacaggat gaggatcgtt tcgcgttctt gactcttcgc gatgtacggg      4800
ccagatatac gcgttgacat tgattattga ctagttatta atagtaatca attacggggt      4860
cattagttca tagcccatat atggagttcc gctcgagcaa aggcgcgcca aaaaagcatg      4920
cggccgcgca ggaacccccta gtgatggagt tggccactcc ctctctgcgc gctcgctcgc      4980
tcactgaggc cgggcgacca aaggtcgccc gacgcccggg ctttgcccgg gcggcctcag      5040
tgagcgagcg agcgcgcagc tgcctgcagg acatgtgagc aaaaggccag caaaaggcca      5100
ggaaccgtaa aaaggccgcg ttgctggcgt ttttccatag gctccgcccc cctgacgagc      5160
atcacaaaaa tcgacgctca agtcagaggt ggcgaaaccc gacaggacta taaagatacc      5220
aggcgtttcc ccctggaagc tccctcgtgc gctctcctgt tccgaccctg ccgcttaccg      5280
gatacctgtc cgcctttctc ccttcgggaa gcgtggcgct ttctcatagc tcacgctgta      5340
ggtatctcag ttcggtgtag gtcgttcgct ccaagctggg ctgtgtgcac gaaccccccg      5400
ttcagcccga ccgctgcgcc ttatccggta actatcgtct tgagtccaac ccggtaagac      5460
acgacttatc gccactggca gcagccactg gtaacaggat tagcagagcg aggtatgtag      5520
gcggtgctac agagttcttg aagtggtggc ctaactacgg ctacactaga agaacagtat      5580
ttggtatctg cgctctgctg aagccagtta ccttcggaaa aagagttggt agctcttgat      5640
ccggcaaaca aaccaccgct ggtagcggtg gtttttttgt ttgcaagcag cagattacgc      5700
gcagaaaaaa aggatctcaa gaagatcctt tgatcttttc tacggggtct gacgctcagt      5760
ggaacgaaaa ctcacgttaa gggattttgg tcatgagatt atcaaaaagg atcttcacct      5820
agatcctttt aaattaaaaa tgaagtttta atcaatcta agtatatat gagtaaactt      5880 ggtctgacag ttagaaaaac tcatcgagca tcaaatgaaa ctgcaattta ttcatatcag      5940
gattatcaat accatatttt tgaaaaagcc gtttctgtaa tgaaggagaa aactcaccga      6000
ggcagttcca taggatggca agatcctggt atcggtctgc gattccgact cgtccaacat      6060
caatacaacc tattaatttc ccctcgtcaa aaataaggtt atcaagtgag aaatcaccat      6120
gagtgacgac tgaatccggt gagaatggca aaagtttatg catttctttc cagacttgtt      6180
caacaggcca gccattacgc tcgtcatcaa aatcactcgc atcaaccaaa ccgttattca      6240
ttcgtgattg cgcctgagcg aggcgaaata cgcgatcgct gttaaaagga caattacaaa      6300
caggaatcga gtgcaaccgg cgcaggaaca ctgccagcgc atcaacaata ttttcacctg      6360
aatcaggata ttcttctaat acctggaacg ctgtttttcc ggggatcgca gtggtgagta      6420
accatgcatc atcaggagta cggataaaat gcttgatggt cggaagtggc ataaattccg      6480
```

```
tcagccagtt tagtctgacc atctcatctg taacatcatt ggcaacgcta cctttgccat        6540
gtttcagaaa caactctggc gcatcgggct tcccatacaa gcgatagatt gtcgcacctg        6600
attgcccgac attatcgcga gcccatttat acccatataa atcagcatcc atgttggaat        6660
ttaatcgcgg cctcgacgtt tcccgttgaa tatggctcat actcttcctt tttcaatatt        6720
attgaagcat ttatcagggt tattgtctca tgacattaac ctataaaaat aggcgtatca        6780
cgaggccctt tcgtctcgcg cgtttcggtg atgacggtga aaacctctga cacatgcagc        6840
tcccggagac ggtcacagct tgtctgtaag cggatgccgg gagcagacaa gcccgtcagg        6900
gcgcgtcagc gggtgttggc gggtgtcggg gctggcttaa ctatgcggca tcagagcaga        6960
ttgtactgag agtgcaccat aaaattgtaa acgttaatat tttgttaaaa ttcgcgttaa        7020 attttgtta aatcagctca tttttttaacc aataggccga aatcggcaaa atcccttata        7080
aatcaaaaga atagcccgag ataggggttga gtgttgttcc agtttggaac aagagtccac       7140
tattaaagaa cgtggactcc aacgtcaaag        7170
```

```
<210> SEQ ID NO 8
<211> LENGTH: 296
<212> TYPE: DNA
<213> ORGANISM: Artificial Sequence
<220> FEATURE:
<223> OTHER INFORMATION: Synthetic Polynucleotide

<400> SEQUENCE: 8
ggaaaggaaa ggtcatcgtc tgtttaattt ccacccccag ctctggactt ccagcattag         60
ctcgccgggc ctcagctgtt gtacacacac ggcgagggggg gaggggaggg cggaggcgcg       120
gaggaggggc cggctgggag gaatctgggc gtcctgccgc gcatgcgcct tgcctgagca       180
acaagtgggc tccacagagg aagtgtaaag gggagggggga agaactggtg cagagcatgg       240
cggtgacgtc agcgctccgc ccgggcggca tcccgcgcgg ccaagccggg gacagc          296
```

```
<210> SEQ ID NO 9
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 9
gctgggggga agggtagcgc actctgaatt catttagctc tatcgttgaa gcccgggttc         60
ctagatcagg gcacaaaaac aaatagaaaa gacaatttct ggaagattgg aaaacagcta       120
attttgcagg tgcttcggca tcagtggtgg cgatgaattt aacatccatg ccggggggga       180
taaggttcaa ccgcagatga aatggttaat accttatacg aaattcacgg cgaaaaatcc       240
tgaaacagga catttaaatt cactgccgag gcttgggggt ggggtgggga gcagggatcg       300
gaaacgacgc tagtggttct taaatgcgtt tttacttggg aatgcccggc agggaaagga       360
aaggtcatcg tctgtttaat ttccacccccc agctctggac ttccagcatt agctcgccgg       420
gcctcagctg ttgtacacac acggcgaggg gggagggggag ggcggaggcg cggaggaggg       480
gccggctggg aggaatctgg gcgtcctgcc gcgcatgcgc cttgcctgag caacaagtgg       540
gctccacaga ggaagtgtaa aggggagggg gaagaactgg tgcagagcat ggcggtgacg       600
tcagcgctcc gcccgggcgg catcccgcgc ggccaagccg gggacagc                648
```

```
<210> SEQ ID NO 10
<211> LENGTH: 1034
```

-continued

```
<212> TYPE: DNA
<213> ORGANISM: Artificial Sequence
<220> FEATURE:
<223> OTHER INFORMATION: Synthetic Polynucleotide

<400> SEQUENCE: 10
cgaggcagag gttgcagtga gccgagatcg cgccattttg cactccagcc tgggcgacag        60
agcaagactc cgtcttaaaa aaaaaaaaaa aaaaaaatca cggccttgtt ccgccttctg       120
gggcaacatg gagtgagatc acagcgcctg agaaagaact ttgaaaactg cggctgtgct       180
ttacaaaaat gtatcagtat tattaaatgc tgcctccacc ttttaaaaat caaactctag       240
aaaaaacact cacctgtttg gcctctccgg cccctccccc tccctgccct gaactgcagc       300
tgtgcgcagc cagttgcctg ttttccttaa aggcctcggg gtgctcgtat cttcttcaga       360
cgttcagcca aaatttttaa agtgcggctg ggggaaggg tagcgcactc tgaattcatt       420
tagctctatc gttgaagccc gggttcctag atcagggcac aaaaacaaat agaaaagaca       480
atttctggaa gattggaaaa cagctaattt tgcaggtgct tcggcatcag tggtggcgat       540
gaatttaaca tccatgccgg gggggataag gttcaaccgc agatgaaatg gttaatacct       600
tatacgaaat tcacggcgaa aaatcctgaa acaggacatt taaattcact gccgaggctt       660
gggggtgggg tggggagcag ggatcggaaa cgacgctagt ggttcttaaa tgcgttttta       720
cttgggaatg cccggcaggg aaaggaaagg tcatcgtctg tttaatttcc accccagct        780 ctggacttcc agcattagct cgccgggcct cagctgttgt acacacacgg cgaggggga        840 ggggagggcg gaggcgcgga ggagggccg gctgggagga atctgggcgt cctgccgcgc        900
atgcgccttg cctgagcaac aagtgggctc cacagaggaa gtgtaaaggg gaggggaag        960 aactggtgca gagcatggcg gtgacgtcag cgctccgccc gggcggcatc ccgcgcggcc      1020
aagccgggga cagc                                                        1034
```

MATERIALS AND METHODS FOR THE TREATMENT OF DISORDERS ASSOCIATED WITH THE IRF2BPL GENE

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: 54846_Seqlisting.txt; Size: 43,149 bytes; Created: Oct. 19, 2020.

FIELD OF THE INVENTION

The disclosure provides gene therapy vectors, such as adeno-associated virus (AAV), designed for treatment of disorders caused by mutation in the Interferon regulatory factor 2 binding protein like (IRF2BPL). The disclosed AAV provide a healthy copy of the IRF2BPL cDNA able to produce the functional protein.

BACKGROUND

The Interferon Regulatory Factor 2 Binding Protein Like (IRF2BPL) gene encodes a member of the IRF2BP family of transcriptional regulators. The deduced 796-amino acid protein has a calculated molecular mass of 82.7 kD. It is proline-rich and contains N-terminal polyglutamine and polyalanine tracts, a C-terminal C3HC4-type ring finger domain, and 2 putative transmembrane domains. It also has a potential nuclear targeting signal, an endoplasmic reticulum retention signal, 3 possible PEST sequences, and putative sites for phosphorylation, N-glycosylation, and amidation. RT-PCR analysis of human tissues detected strong expression in heart, moderate expression in skeletal muscle and pancreas, and weak expression in brain, kidney, liver, testis, thyroid, and lymphocytes. There are two mammalian paralogs IRF2BP1 and IRF2BP2 that share two highly conserved domains. Using DNA microarrays, Heger et al. (2007) found that expression of IRF2BPL, which they termed Eap1, increased in the medial basal hypothalamus, but not cerebral cortex, of female rhesus monkeys at early puberty and increased further at mid-puberty. Female mice underwent a similar increase of Eap1 expression in hypothalamus, but not cortex, during puberty. The function of this protein in unknown, and until recently it was not associated to a Mendelian disease.

Mutations in the IRF2BPL gene were found to be associated with NEDAMSS (neurodevelopmental disorder with regression, abnormal movements, loss of speech, and seizures) disease in children. NEDAMSS exhibits autosomal dominant inheritance that has onset during childhood and is a progressive disorder. There are no current therapies for NEDAMSS and any other IRF2BPL disorders and there is a need to develop such therapies.

SUMMARY

In one aspect, described herein is a polynucleotide comprising (a) one or more regulatory control elements; and (b) an Interferon regulatory factor 2 binding protein like (IRF2BPL) cDNA sequence. In some embodiments, the regulatory control element is pIRF promoter, p546 promoter comprising a nucleotide sequence set forth in SEQ ID NO: 5 or CBA promoter comprising a nucleotide sequence set forth in SEQ ID NO: 6, or fragments thereof which retain regulatory control or promoter activity. In some embodiments, the IRF2BPL cDNA comprises the polynucleotide sequence set forth in SEQ ID NO: 1.

In another aspect, described herein is a recombinant adeno-associated virus (rAAV) having a genome comprising a polynucleotide sequence described herein. In some embodiments, the rAAV is of the serotype AAV1, AAV2, AAV3, AAV4, AAV5, AAV6, AAV7, AAV8, AAV9, AAVRH10, AAVRH74, AAV11, AAV12, AAV13, or Anc80, AAV7m8 and their derivatives.

In some embodiments, the genome of the rAAV comprises a pIRF promoter fragment and an IRF2BPL cDNA. The nucleotide sequence of the pIRF promoter fragment is 1034 base pairs and set out as SEQ ID NO: 10. For example, the genome of the rAAV comprises a pIRF promoter comprising nucleotides 1-1034 of the pIRF (SEQ ID NO: 10), or a promoter fragment comprising nucleotides 386-1034 of the pIRF (SEQ ID NO: 9), or a promoter fragment comprising nucleotides 738-1034 of the pIRF (SEQ ID NO: 8).

In some embodiments, the genome of the rAAV comprises a p546 promoter and an IRF2BPL cDNA.

In some embodiments, the genome of the rAAV comprises a CBA promoter and an IRF2BPL cDNA.

In some embodiments, the genome of the rAAV comprises a pIRF promoter fragment, a p546 promoter and an IRF2BPL cDNA, wherein the promoter retains promoter activity.

In an exemplary embodiment, the genome of the rAAV comprises nucleotides 342 to 5299 of SEQ ID NO: 3, or nucleotides 342 to 5031 of SEQ ID NO: 4, or nucleotides 342 to 5070 of SEQ ID NO: 7.

In another aspect, described herein is an rAAV particle comprising an rAAV described herein.

Methods of treating an Interferon regulatory factor 2 binding protein like (IRF2BPL)-related disorder in a subject in need thereof comprising administering an rAAV or an rAAV particle described herein are specifically contemplated. An IRF2BPL-related disorder is a neurological disorder that is associated with the presence of a mutation in the IRF2BPL gene. In some embodiments, the IRF2BPL-related disorder comprises NEDAMSS (neurodevelopmental disorder with regression, abnormal movements, loss of speech, and seizures) or other neurological disorders including, but not limited to, epilepsy, schizophrenia and neuropathy.

In another aspect, described herein is the use an rAAV or an rAAV particle described herein in the preparation of a medicament for the treatment of an Interferon regulatory factor 2 binding protein like (IRF2BPL)-related disorder, such as NEDAMSS.

In another aspect, described herein is a composition comprising an rAAV or an rAAV particle described herein for the treatment of an Interferon regulatory factor 2 binding protein like (IRF2BPL)-related disorder, such as NEDAMSS.

BRIEF DESCRIPTION OF THE FIGURES

FIG. 2A demonstrates IRF2BPL protein expression detected by immunofluorescence. FIG. 2B provides IRF2BPL protein expression detected by Western blot (n=3). The data indicates no major differences in protein expression levels between healthy controls and NEDAMSS patients except for one patient (P3) which shows a reduction.

Figure 2:
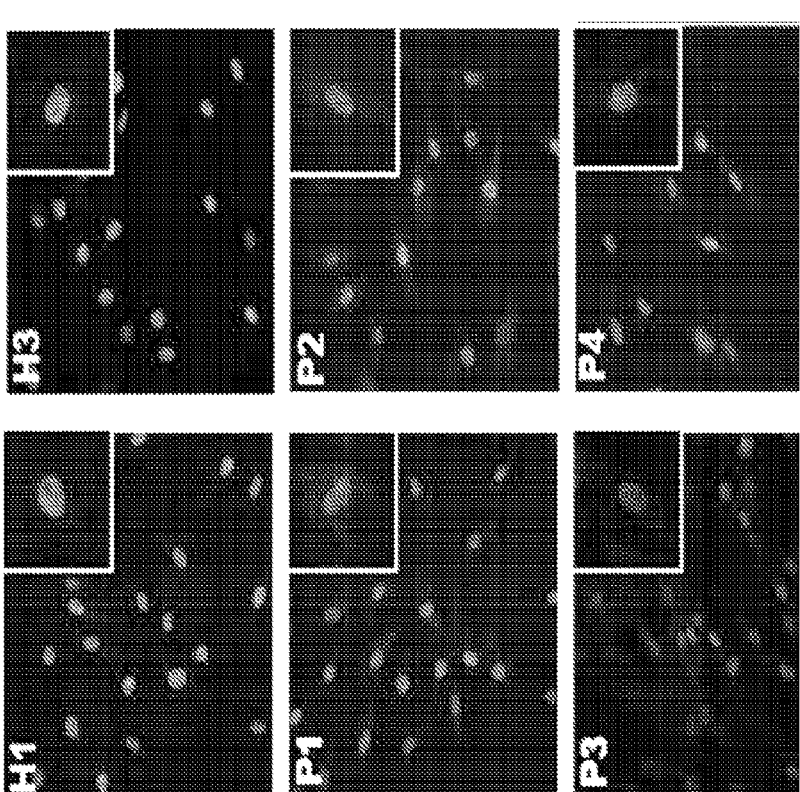
FIG. 2A-2B provides data demonstrating the expression of Interferon regulatory factor 2 binding protein like (IRF2BPL) in fibroblasts isolated from healthy individuals and patients suffering from NEDAMSS (denoted as "disease").
Figure 3:
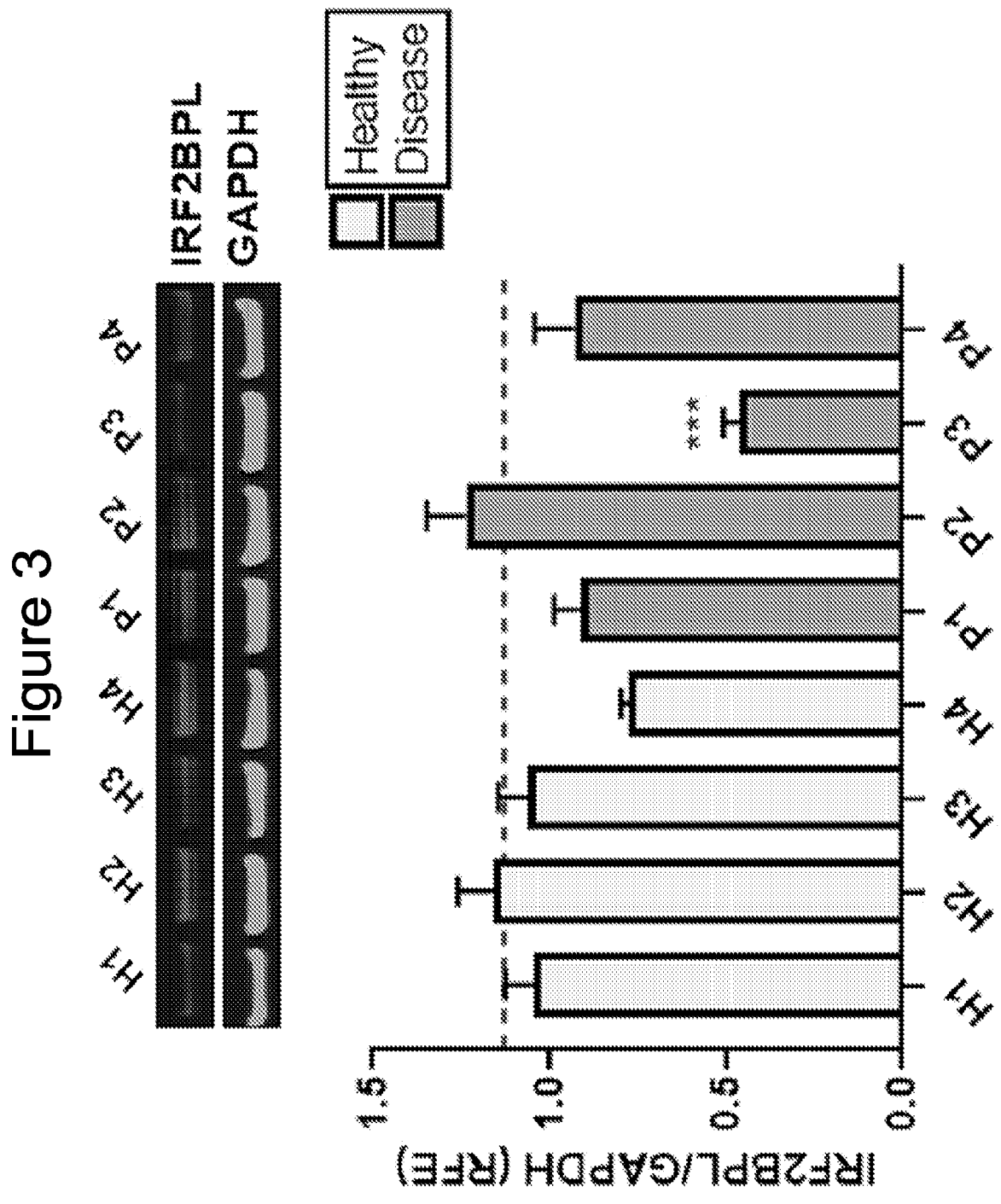

FIG. 3 provides graphs showing the expression of IRF2BPL protein in astrocytes (iAST) induced from fibroblasts isolated from healthy individuals and patients suffering from NEDAMSS. No major differences were seen in overall levels of protein expression except for the same patient cell line in which already the fibroblasts showed a decrease in IRF2BPL expression in FIG. 2 (P3).

Figure 4A:
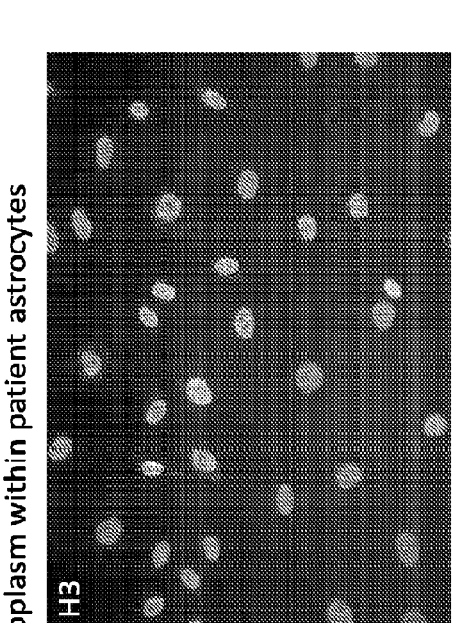
Figure 4A:
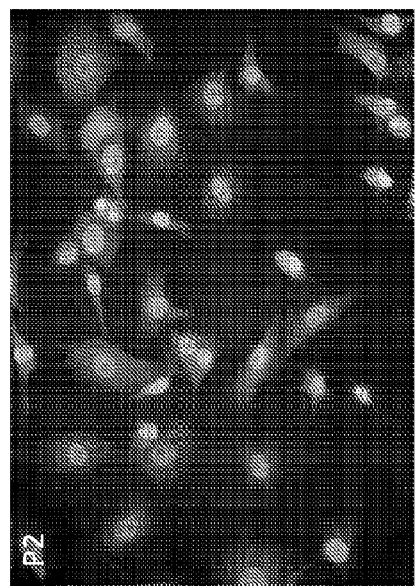
Figure 4A:
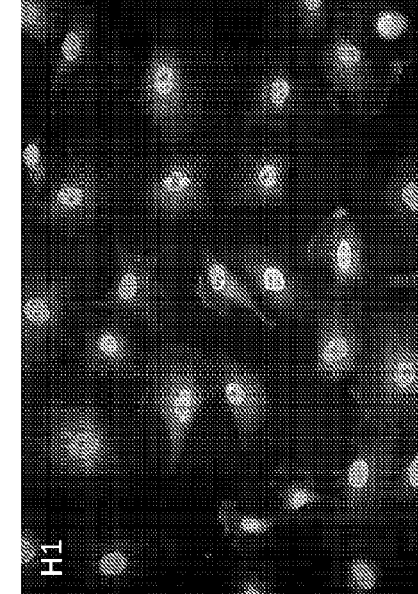
Figure 4A:
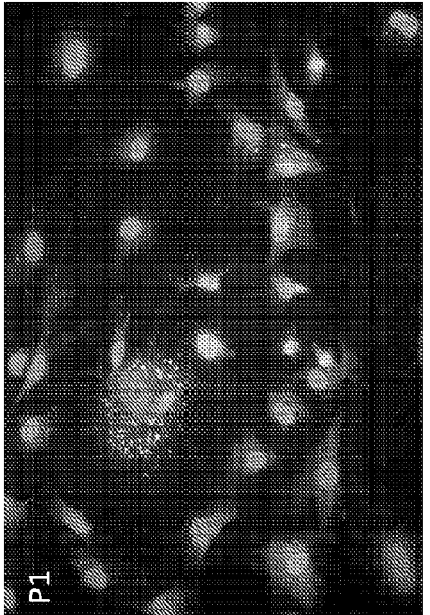
Figure 4B:
Figure 4B:
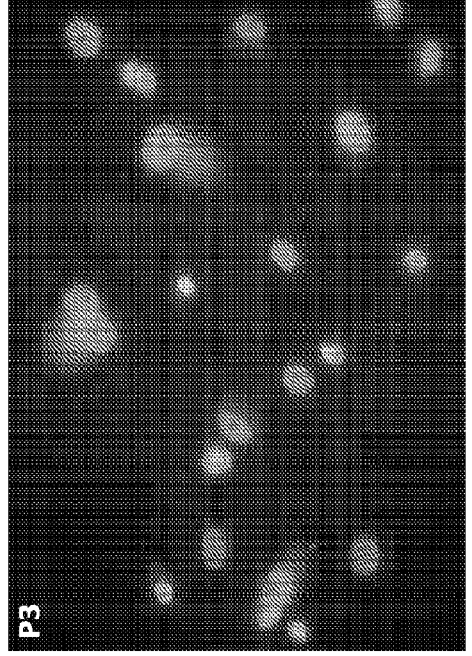

FIGS. 4A and 4B are representative images showing that IRF2BPL aberrantly accumulates in the cytoplasm of iAST from patients suffering from NEDAMSS (P1. P2, P3 and P4). The blue stain is DAPI and the red staining is IRF2BPL, when overlapping, the stain appears purple.

Figure 5:
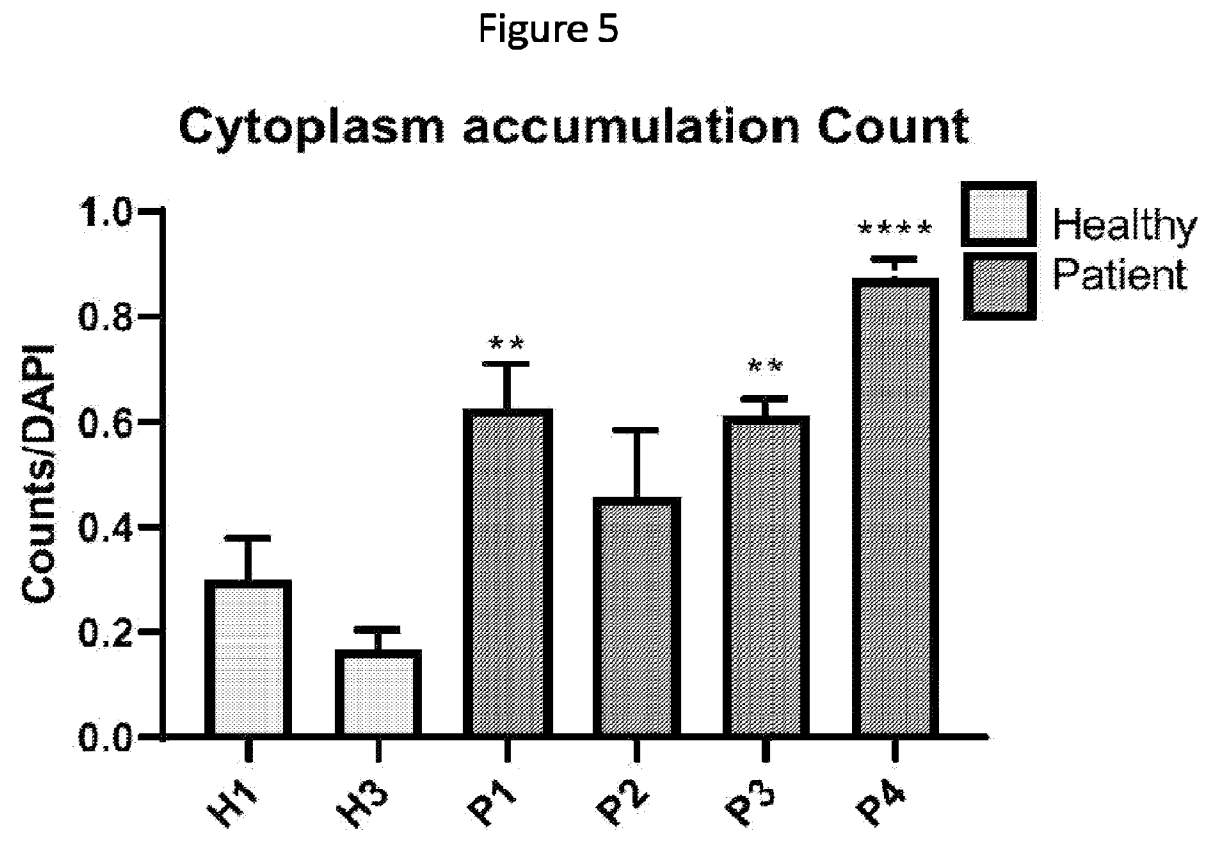

FIG. 5 provides a graph showing the normalized ratio of number of cells with cytoplasm accumulation of IRF2BPL in fibroblasts to the DAPI counts (n=3).

Figure 6:
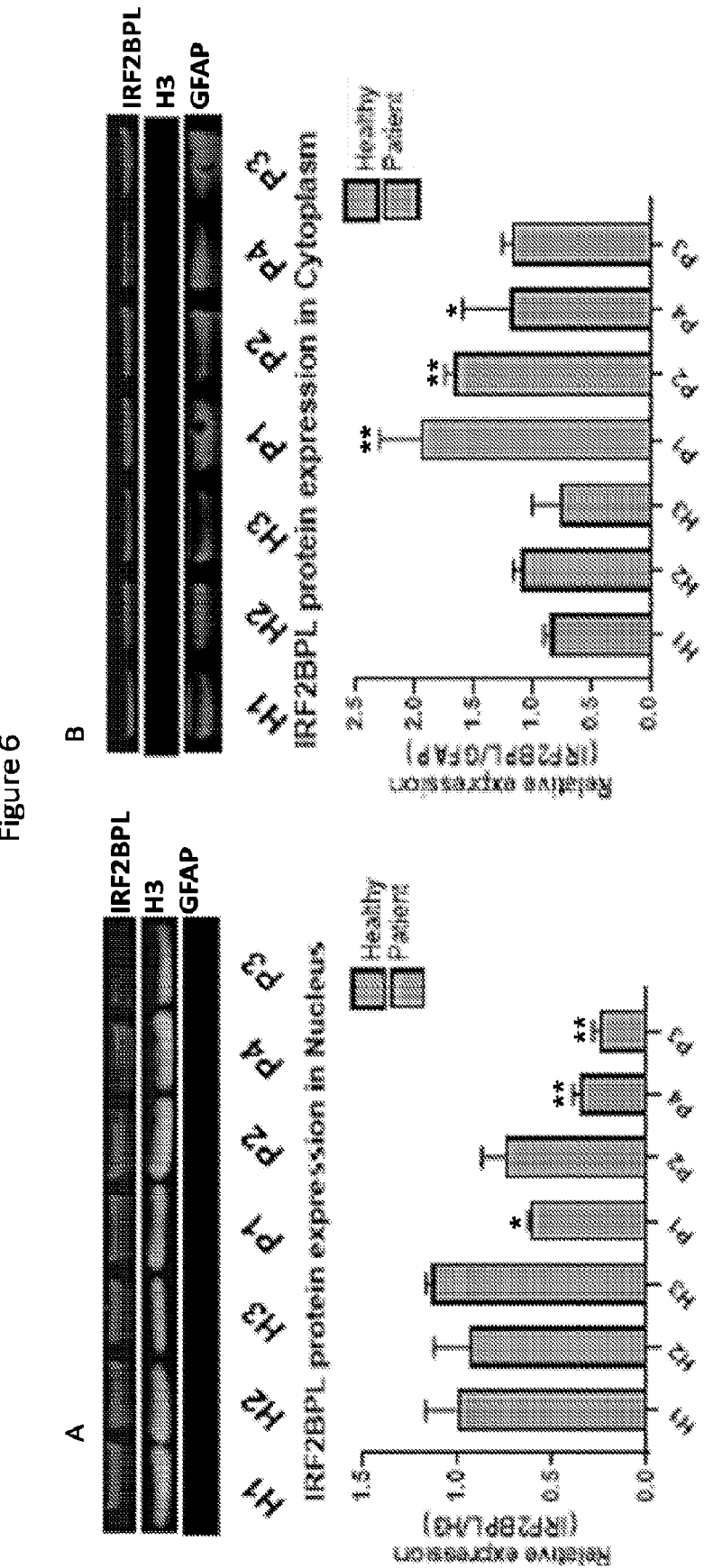

FIG. 6 provides graphs showing IRF2BPL protein expression in nucleus (FIG. 6A) and cytoplasm (FIG. 6B) extracts from patients and control astrocyte (n=3). Also supporting the increase in accumulation in the cytoplasm in patient iASTs and a decrease in nuclear localization.

Figure 7:
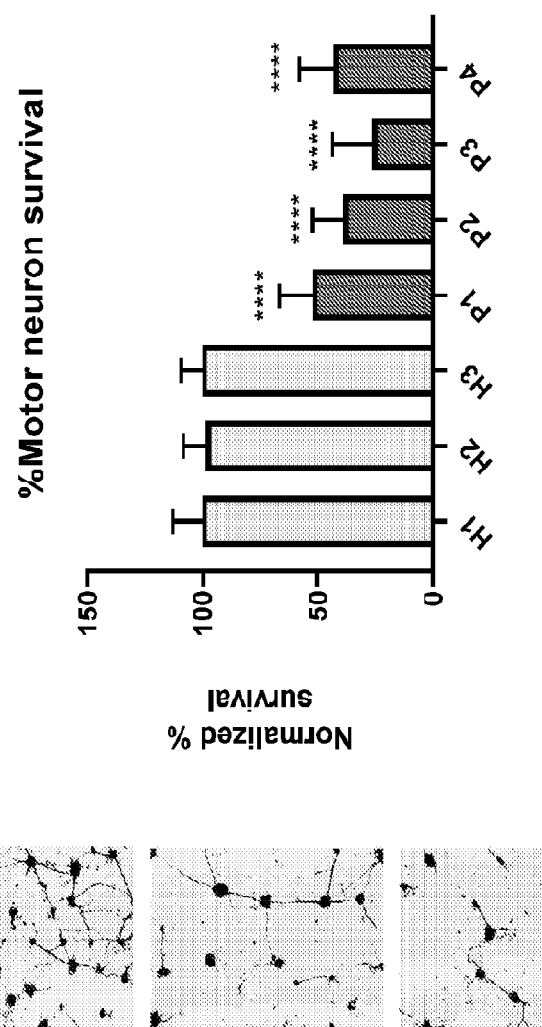

FIG. 7A-7B provides representative images and quantification showing mouse motor neuron survival after three days co-culture of patient or healthy iASTs with GFP+ motor neurons (in black), n=4.

Figure 8:
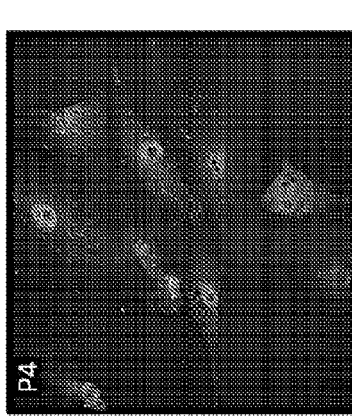
Figure 8:
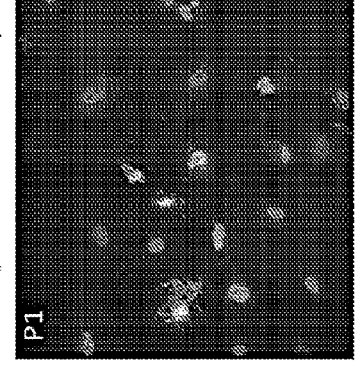
Figure 8:
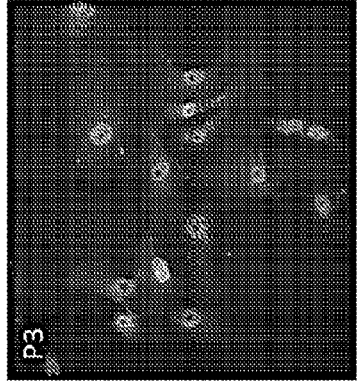
Figure 8:
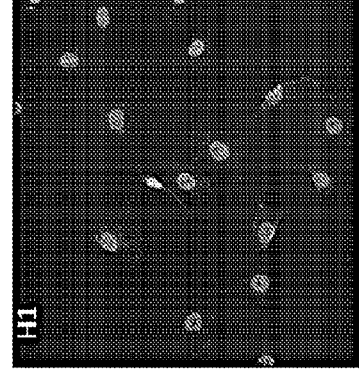
Figure 8:
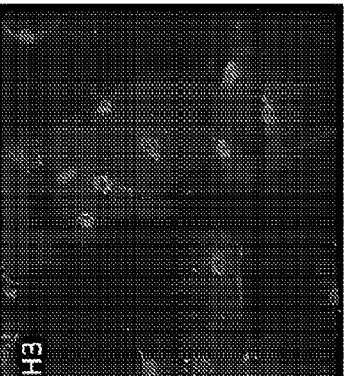

FIG. 8 provides immunofluorescence staining for WNT1 and DAPI in NEDAMSS patient cell lines. WNT1 expression was increased in the NEDAMSS patients.

Figure 9:
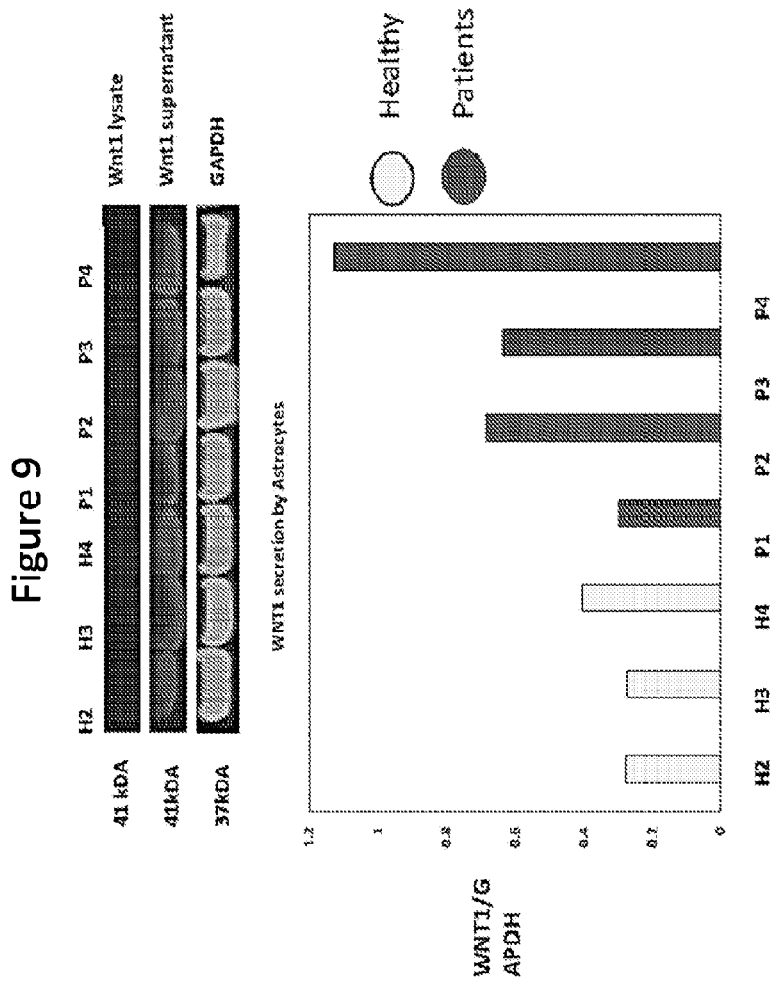

FIG. 9 provides Western blot data measuring WNT1 levels in the lysate and the supernatant in ASTs from healthy and NEDAMSS patients (n=1). The graph demonstrates that the WNT1 expression is increased in the astrocyte supernatants from NEDAMSS patients.

Figure 10A:
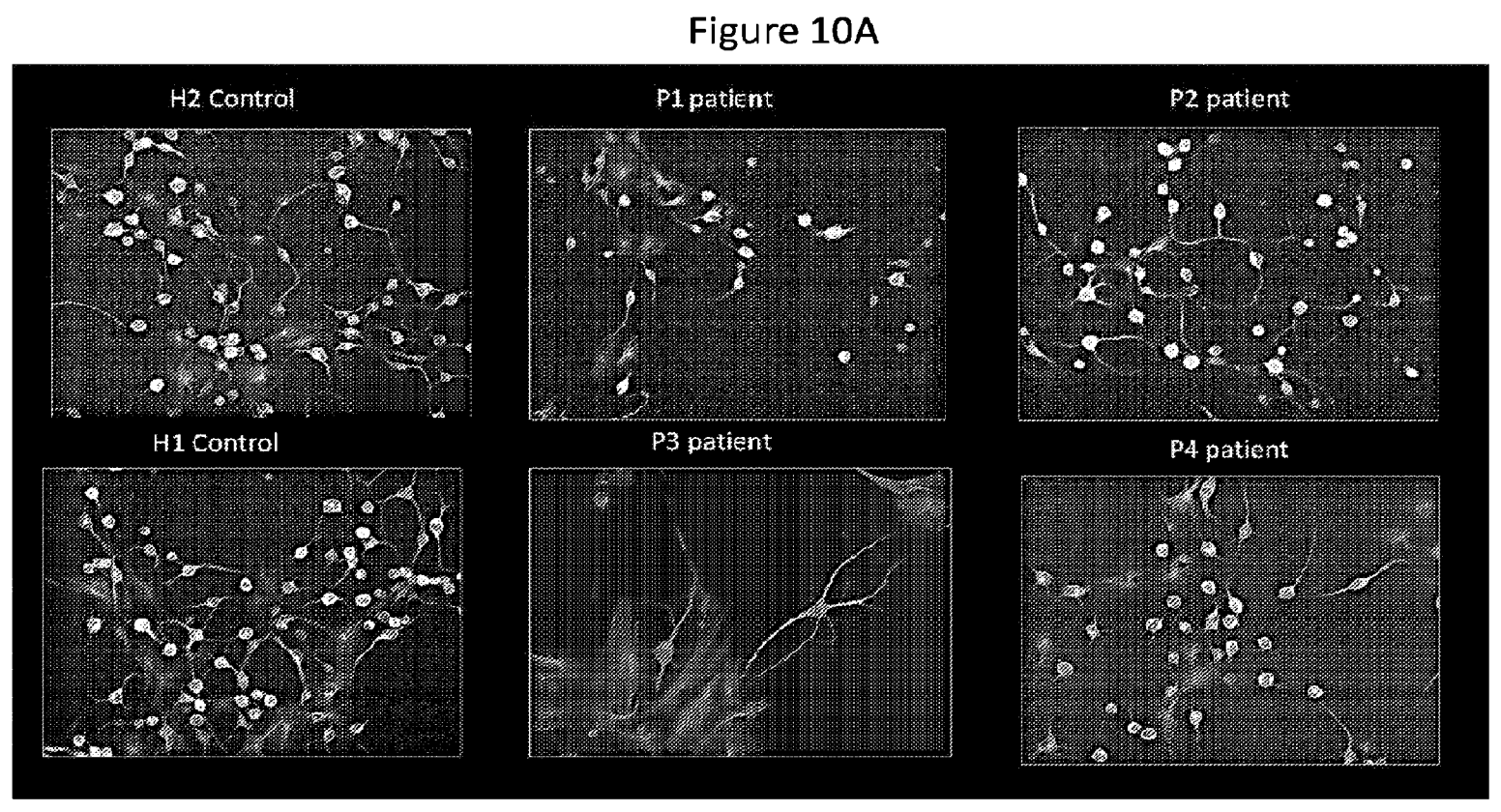
Figure 10B:
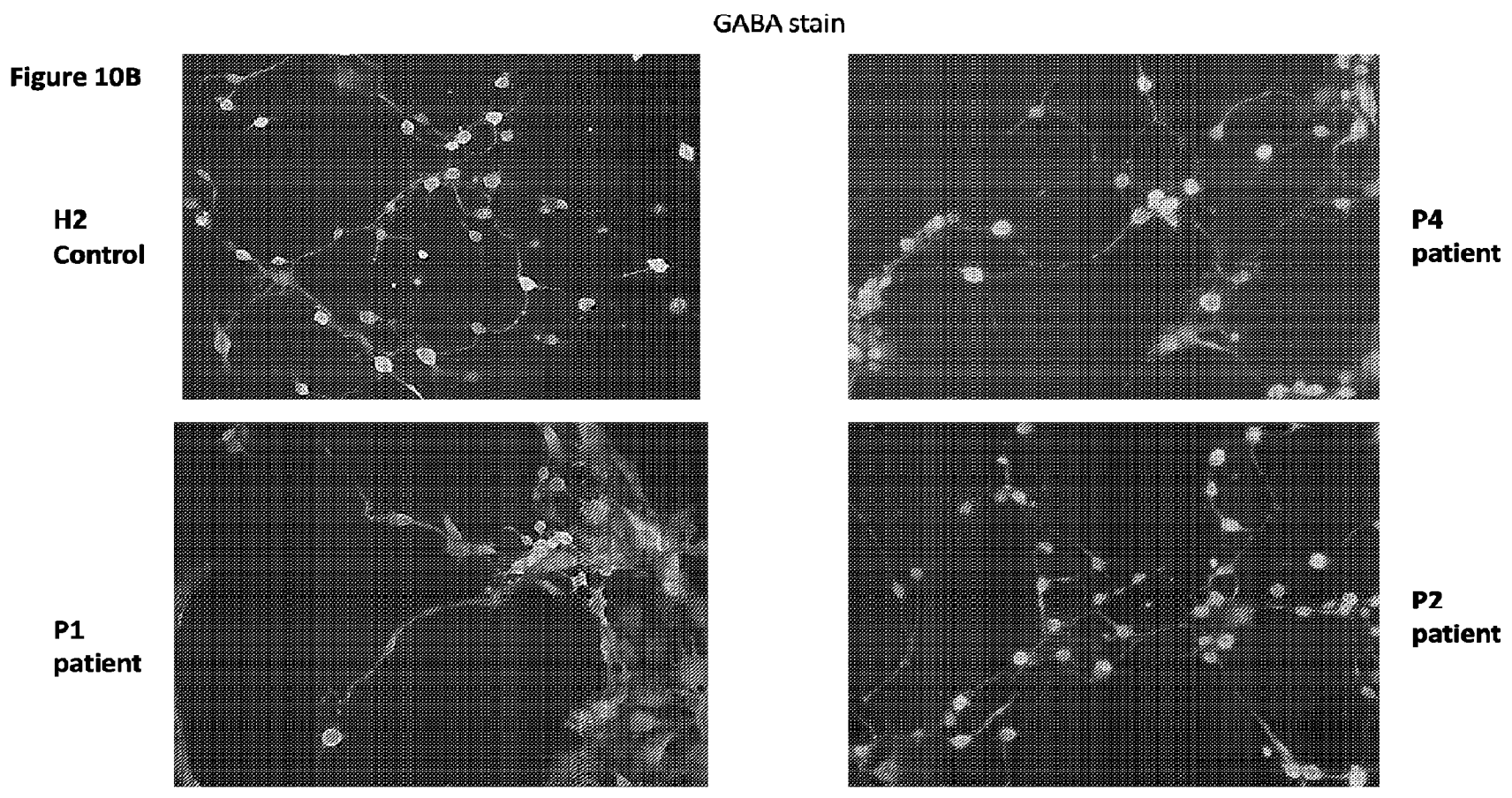

FIGS. 10A and B provide representative images showing that reduced numbers of neurons were found in NEDAMSS patient cell lines compared to healthy controls after direct reprogramming from fibroblasts. FIG. 10A provides staining using the pan-neuronal marker Tuj1, and FIG. 10B provides staining for neuron specific marker GABA. Control refers to neurons induced from a healthy individual.

Figure 11:
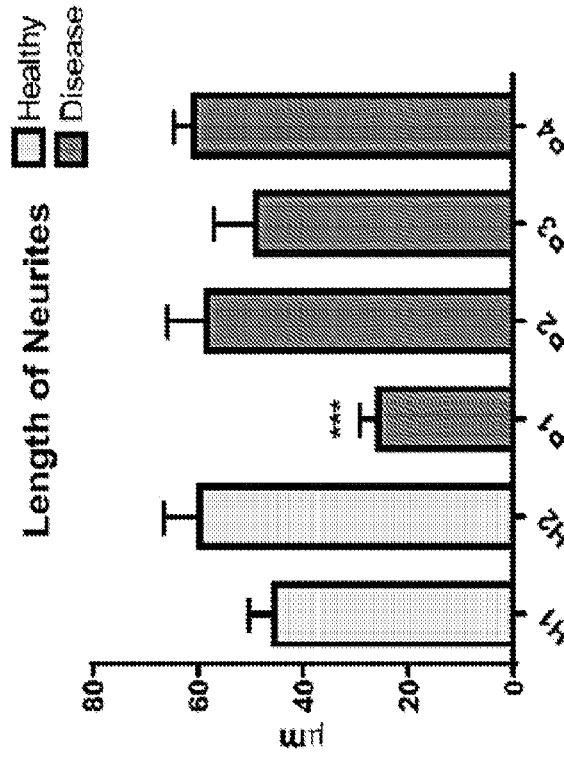
Figure 11:
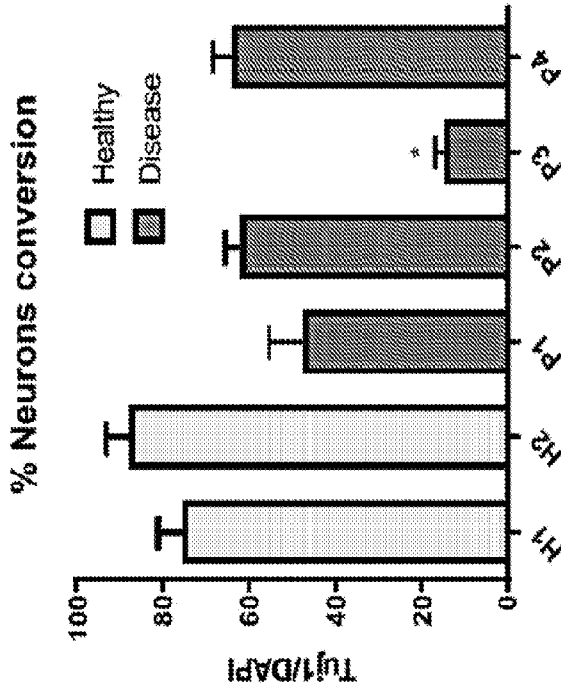

FIG. 11 provides graphs showing the comparison of percentage neuronal conversion rate and the neurite length. Indicating reduced generation of neurons from fibroblasts of NEDAMSS patients.

Figure 12A:
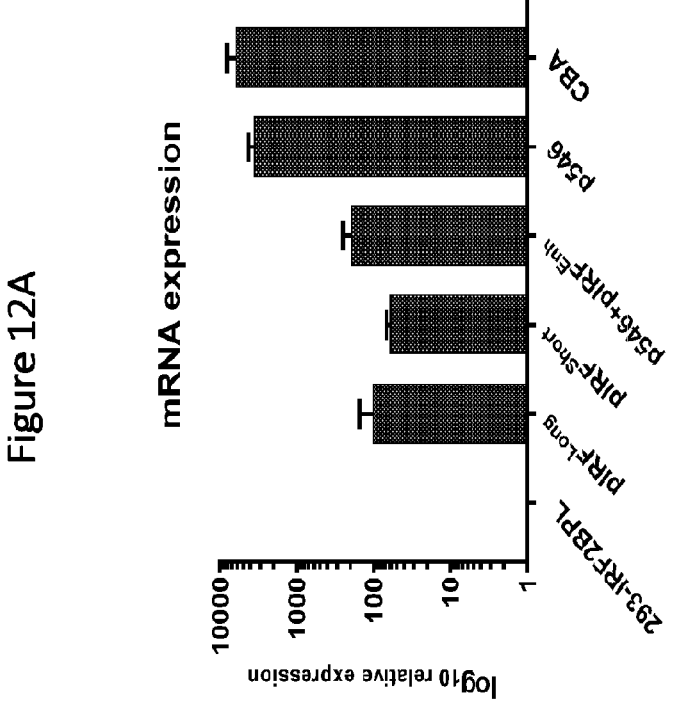

FIGS. 12A and 13B are graphs showing IRF2BPL mRNA (FIG. 12A) and IRF2BPL protein (FIG. 12B) expression between wild-type IRF2BPL levels in HEK-293 and GFP levels as induced by five different promoters.

Figure 13:
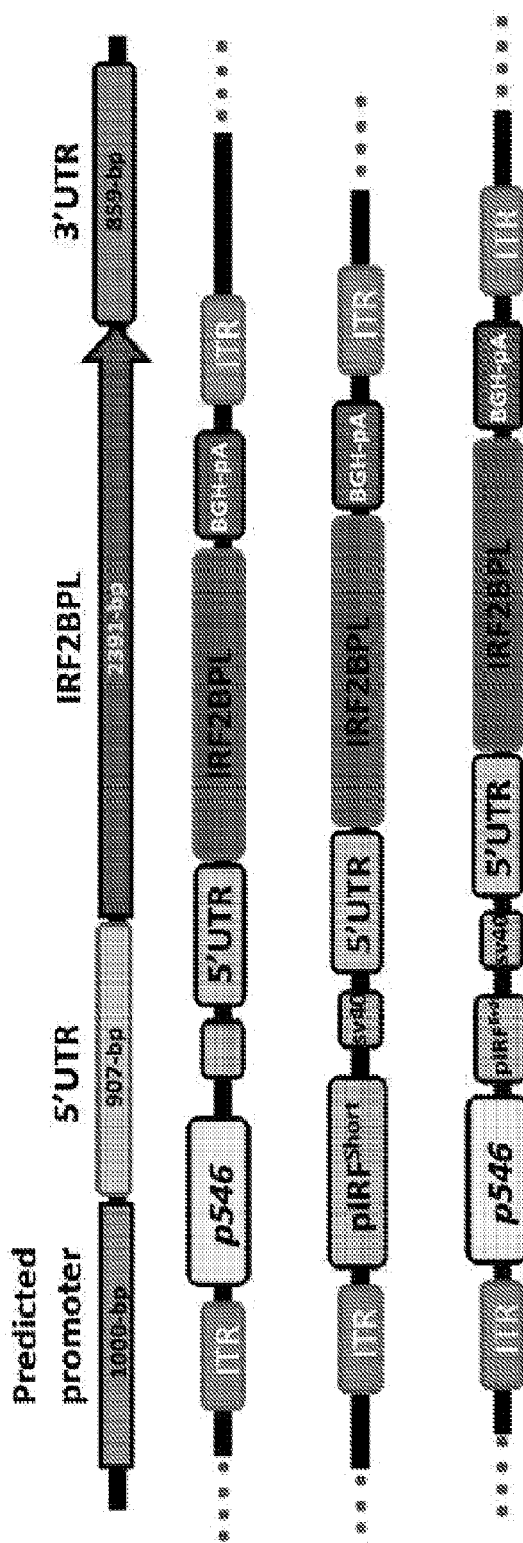

FIG. 13 depicts the strategy for designing three AAV gene therapy vectors encoding the wild type IRE2BPL gene using p546 and truncated variants of the endogenous pIRF promoter.

FIG. 14 provides an annotated sequence of ssAAV9-p546+pIRF$^{ENH}$-5'UTR-IRF2BPL (SEQ ID NO: 3) showing the location of the construct elements.

FIG. 15 provides an annotated sequence of ssAAV9-pIRF$^{SHORT}$-5'UTR-IRF2BPL (SEQ ID NO: 4) showing location of the construct elements.

FIG. 16 provides an annotated sequence of ssAAV9-p546-5'UTR-IRF2BPL SEQ ID NO: 7) showing the location of the construct elements.

DETAILED DESCRIPTION

The Interferon Regulatory Factor 2 Binding Protein Like (IRF2BPL) gene encodes a member of the IRF2BP family of transcriptional regulators.

IRF2BPL is an intron-less gene located at 14q24.23. The transcript is expressed in many organs, including in the central nervous system (CNS) components such as the cerebellum.

IRF2BPL Mutations

The wild-type cDNA sequence of IRF2BPL is set forth in SEQ ID NO: 1. The nucleic acid sequence of the full length IRF2BPL gene is set for the in SEQ ID NO: 2. The in vivo function of IRF2BPL in all species remains largely undefined although previous studies have shown its role in the reproductive cycle in rodents and monkeys. Recently, mutations in this gene were found to be associated with NEDAMSS (neurodevelopmental disorder with regression, abnormal movements, loss of speech, and seizures) disease in children. NEDAMSS exhibits autosomal dominant inheritance. Not much is known regarding the mechanism of this rare disease. A total of 18 patients are known to have this disease so far in the world.

In some embodiments, the IRF2BPL gene in a cell of a diseased subject comprises one or of the following mutations in SEQ ID NO: 1: Q126X, Q127X, E172X, Y173X, R188X, G195V, P372R, K418N, and/or a frame shift mutation at A708 (A708fs).

AAV Gene Therapy

The present disclosure provides for gene therapy vectors, e.g. rAAV vectors, expressing the IRF2BPL gene and methods of treating NEDAMSS (neurodevelopmental disorder with regression, abnormal movements, loss of speech, and seizures).

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cloning of the AAVrh.74 serotype is described in Rodino-Klapac., et al. *Journal of translational medicine* 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° C. to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther*, 8: 659-669 (1997); Kessler et al., *Proc Nat. Acad Sc. USA*, 93: 14082-14087 (1996); and Xiao et al., *J Virol*, 70: 8098-8108 (1996). See also, Chao et al., *Mol Ther*, 2:619-623 (2000) and Chao et al., *Mol Ther*, 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA*, 94: 5804-5809 (1997) and Murphy et al., *Proc Natl Acad Sci USA*, 94: 13921-13926 (1997). Moreover, Lewis et al., *J Virol*, 76: 8769-8775 (2002) demonstrated that skeletal myofibers possess the necessary cellular factors for correct antibody glycosylation, folding, and secretion, indicating that muscle is capable of stable expression of secreted protein therapeutics.

Recombinant AAV genomes of the disclosure comprise nucleic acid molecule of the disclosure and one or more AAV ITRs flanking a nucleic acid molecule. AAV DNA in the rAAV genomes may be from any AAV serotype for which a recombinant virus can be derived including, but not limited to, AAV serotypes (e.g., AAV1, AAV2, AAV3, AAV4, AAV5, AAV6, AAV7, AAV8, AAV9, AAVRH10, AAVRH74, AAV11, AAV12, AAV13, or Anc80, AAV7m8 and their derivatives). Production of pseudotyped rAAV is disclosed in, for example, WO 01/83692. Other types of rAAV variants, for example rAAV with capsid mutations, are also contemplated. See, for example, Marsic et al., *Molecular Therapy*, 22(11): 1900-1909 (2014). As noted in the Background section above, the nucleotide sequences of the genomes of various AAV serotypes are known in the art.

The provided recombinant AAV (i.e., infectious encapsidated rAAV particles) comprise a rAAV genome. The term "rAAV genome" refers to a polynucleotide sequence that is derived from a native AAV genome that has been modified. In some embodiments, the rAAV genome has been modified to remove the native cap and rep genes. In some embodiments, the rAAV genome comprises the endogenous 5' and 3' inverted terminal repeats (ITRs). In some embodiments, the rAAV genome comprises ITRs from an AAV serotype that is different from the AAV serotype from which the AAV genome was derived. In some embodiments, the rAAV genome comprises a transgene of interest flanked on the 5' and 3' ends by inverted terminal repeat (ITR). In some embodiments, the rAAV genome comprises a "gene cassette." In exemplary embodiments, the genomes of both rAAV lack AAV rep and cap DNA, that is, there is no AAV rep or cap DNA between the ITRs of the genomes.

The rAAV genomes provided herein, in some embodiments, comprise one or more AAV ITRs flanking the transgene polynucleotide sequence. The transgene polynucleotide sequence is operatively linked to transcriptional control elements (including, but not limited to, promoters, enhancers and/or polyadenylation signal sequences) that are functional in target cells to form a gene cassette. Examples of promoters are the pIRF promoter (SEQ ID NO: 10), chicken β actin promoter (CBA) comprising the polynucleotide sequence set forth in SEQ ID NO: 6, and the P546 promoter comprising the polynucleotide sequence set forth in SEQ ID NO: 5. Additional promoters are contemplated herein including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter.

Additionally provided herein are a pIRF promoter sequence, a CB promoter sequence, a P546 promoter sequence, and promoter sequences at least: 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence of the pIRF (SEQ ID NO: 10), CBA (SEQ ID NO: 6) or P546 (SEQ ID NO: 5) sequence which exhibit transcription promoting activity.

Other examples of transcription control elements are tissue specific control elements, for example, promoters that allow expression specifically within neurons or specifically within astrocytes. Examples include neuron specific enolase and glial fibrillary acidic protein promoters. Inducible promoters are also contemplated. Non-limiting examples of inducible promoters include, but are not limited to a metallothionine promoter, a glucocorticoid promoter, a progesterone promoter, and a tetracycline-regulated promoter. The gene cassette may also include intron sequences to facilitate processing of a transgene RNA transcript when expressed in mammalian cells. One example of such an intron is the SV40 intron.

rAAV genomes provided herein comprises a polynucleotide (SEQ ID NO: 1) encoding IRF2BPL. In some embodiments, the rAAV genomes provided herein comprises a polynucleotide sequence that encodes a polypeptide comprising an amino acid sequence that is at least: 90%, 91%, 92%, 93%, 94%, 95%, 96%, 97%, 98%, or 99% identical to the amino acid sequence encoded by the IRF2BPL cDNA (SEQ ID NO 1).

rAAV genomes provided herein, in some embodiments, a polynucleotide sequence that encodes an IRF2BPL protein and that hybridizes under stringent conditions to the polynucleotide sequence set forth in SEQ ID NO: 1 or the complement thereof.

In exemplary embodiments, the rAAV genomes comprises nucleotides 342 to 5299 of SEQ ID NO: 3, or nucleotides 342 to 5031 of SEQ ID NO: 4, or nucleotides 342 to 5070 of SEQ ID NO: 7. In some embodiments, the rAAV genomes provided herein comprise a polynucleotide sequences that is at least: 90%, 91%, 92%, 93%, 94%, 95%, 96%, 97%, 98%, or 99% identical to nucleotides 342 to 5299 of SEQ ID NO: 3, or nucleotides 342 to 5031 of SEQ ID NO: 4, or nucleotides 342 to 5070 of SEQ ID NO: 7. In other embodiments, the rAAV genomes provided herein comprise a polynucleotide sequence that hybridizes under stringent conditions to nucleotides 342 to 5299 of SEQ ID NO: 3, or nucleotides 342 to 5031 of SEQ ID NO: 4, or nucleotides 342 to 5070 of SEQ ID NO: 7.

DNA plasmids of the disclosure comprise rAAV genomes of the disclosure. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-9, AAV-1, AAV-2, AAV-3, AAV-4, AAV-5, AAV-6, AAV-7, AAVrh.74, AAV-8, AAV-10, AAV-11, AAV-12 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, *Proc. Natl. Acad. S6. USA,* 79:2077-2081), addition of synthetic linkers containing restriction endonuclease cleavage sites (Laughlin et al., 1983, *Gene,* 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., *Mol. Cell. Biol.* 4:2072 (1984); Hermonat et al., *Proc. Natl. Acad. Sci. USA,* 81:6466 (1984); Tratschin et al., *Mol. Cell. Biol.* 5:3251 (1985); McLaughlin et al., *J. Virol.,* 62:1963 (1988); and Lebkowski et al., *Mol. Cell. Biol.,* 7:349 (1988). Samulski et al., *J. Virol.,* 63:3822-3828 (1989); U.S. Pat. No. 5,173,414; WO 95/13365 and corresponding U.S. Pat. No. 5,658,776; WO 95/13392; WO 96/17947; PCT/U598/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. *Vaccine* 13:1244-1250 (1995); Paul et al. *Human Gene Therapy* 4:609-615 (1993); Clark et al. *Gene Therapy* 3:1124-1132 (1996); U.S. Pat. Nos. 5,786,211; 5,871,982; and 6,258,595. The foregoing documents are hereby incorporated by reference in their entirety herein, with particular emphasis on those sections of the documents relating to rAAV production.

The disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

Compositions provided herein comprise rAAV and a pharmaceutically acceptable excipient or excipients. Acceptable excipients are nontoxic to recipients and are preferably inert at the dosages and concentrations employed, and include, but are not limited to, buffers such as phosphate [e.g., phosphate-buffered saline (PBS)], citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, copolymers such as poloxamer 188, pluronics (e.g., Pluronic F68) or polyethylene glycol (PEG). Compositions provided herein can comprise a pharmaceutically acceptable aqueous excipient containing a non-ionic, low-osmolar compound such as iobitridol, iohexol, iomeprol, iopamidol, iopentol, iopromide, ioversol, or ioxilan, where the aqueous excipient containing the non-ionic, low-osmolar compound can have one or more of the following characteristics: about 180 mgI/mL, an osmolality by vapor-pressure osmometry of about 322 mOsm/kg water, an osmolarity of about 273 mOsm/L, an absolute viscosity of about 2.3 cp at 20° C. and about 1.5 cp at 37° C., and a specific gravity of about 1.164 at 37° C. Exemplary compositions comprise about 20 to 40% non-ionic, low-osmolar compound or contrast agent or about 25% to about 35% non-ionic, low-osmolar compound. An exemplary composition comprises scAAV or rAAV viral particles formulated in 20 mM Tris (pH8.0), 1 mM MgCl$_2$, 200 mM NaCl, 0.001% poloxamer 188 and about 25% to about 35% non-ionic, low-osmolar compound. Another exemplary composition comprises scAAV formulated in and 1×PBS and 0.001% Pluronic F68.

Dosages of rAAV to be administered in methods of the disclosure will vary depending, for example, on the particular rAAV, the mode of administration, the time of administration, the treatment goal, the individual, and the cell type(s) being targeted, and may be determined by methods standard in the art. Dosages may be expressed in units of viral genomes (vg). Dosages contemplated herein include about 1×10$^7$, 1×10$^8$, 1×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$, 1×10$^{11}$, about 1×10$^{12}$, about 1×10$^{13}$, about 1.1×10$^{13}$, about 1.2× 10$^{13}$, about 1.3×10$^{13}$, about 1.5×10$^{13}$, about 2×10$^{13}$, about 2.5×10$^{13}$, about 3×10$^{13}$, about 3.5×10$^{13}$, about 4×10$^{13}$, about 4.5×10$^{13}$, about 5×10$^{13}$, about 6×10$^{13}$, about 1×10$^{14}$, about 2×10$^{14}$, about 3×10$^{14}$, about 4×10$^{14}$ about 5×10$^{14}$, about 1×10$^{15}$, to about 1×10$^{16}$, or more total viral genomes. Dosages of about 1×10$^9$ to about 1×10$^{10}$, about 5×10$^9$ to about 5×10$^{10}$, about 1×10$_{10}$ to about 1×10$^{11}$, about 1×10$^{11}$ to about 1×10$^{15}$ vg, about 1×10$^{12}$ to about 1×10$^{15}$ vg, about 1×10$^{12}$ to about 1×10$^{14}$ vg, about 1×10$^{13}$ to about 6×10$^{14}$ vg, and about 6×10$^{13}$ to about 1.0×10$^{14}$ vg are also contemplated. One dose exemplified herein is 6×10$^{13}$ vg. Another dose exemplified herein is 1.5×10$^{13}$ vg.

Methods of transducing a target cell with rAAV, in vivo or in vitro, are contemplated by the disclosure. The in vivo methods comprise the step of administering an effective dose, or effective multiple doses, of a composition comprising a rAAV of the disclosure to an animal (including a human being) in need thereof. If the dose is administered prior to development of a disorder/disease, the administration is prophylactic. If the dose is administered after the development of a disorder/disease, the administration is therapeutic. In embodiments of the disclosure, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the disclosure is NEDAMSS.

Combination therapies are also contemplated by the disclosure. Combination as used herein includes both simultaneous treatment and sequential treatments. Combinations of methods of the disclosure with standard medical treatments are specifically contemplated, as are combinations with novel therapies.

Administration of an effective dose of the compositions may be by routes standard in the art including, but not limited to, intramuscular, parenteral, intrathecal or other methods of accessing the cerborspinal fluid, intracerebroventricular, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the disclosure may be chosen and/or matched by those skilled in the art taking into account the infection and/or disease state being treated and the target cells/tissue(s) that are to express the wild type IRF2BPL protein.

The disclosure provides for local administration and systemic administration of an effective dose of rAAV and compositions of the disclosure. For example, systemic administration is administration into the circulatory system so that the entire body is affected. Systemic administration includes enteral administration such as absorption through the gastrointestinal tract and parenteral administration through injection, infusion or implantation.

Transduction of cells with rAAV of the disclosure results in sustained expression of the IRF2BPL protein. The present disclosure thus provides methods of administering/delivering rAAV which express IRF2BPL protein to an animal, preferably a human being. These methods include transducing cells with one or more rAAV of the present disclosure.

The term "transduction" is used to refer to the administration/delivery of the coding region of the IRF2BPL to a recipient cell either in vivo or in vitro, via a replication-deficient rAAV of the disclosure resulting in expression of IRF2BPL by the recipient cell.

The following EXAMPLES are provided by way of illustration and not limitation. Described numerical ranges are inclusive of each integer value within each range and inclusive of the lowest and highest stated integer.

EXAMPLES

Example 1—Characterization of iAstrocytes from NEDAMSS Patients

Figure 1:
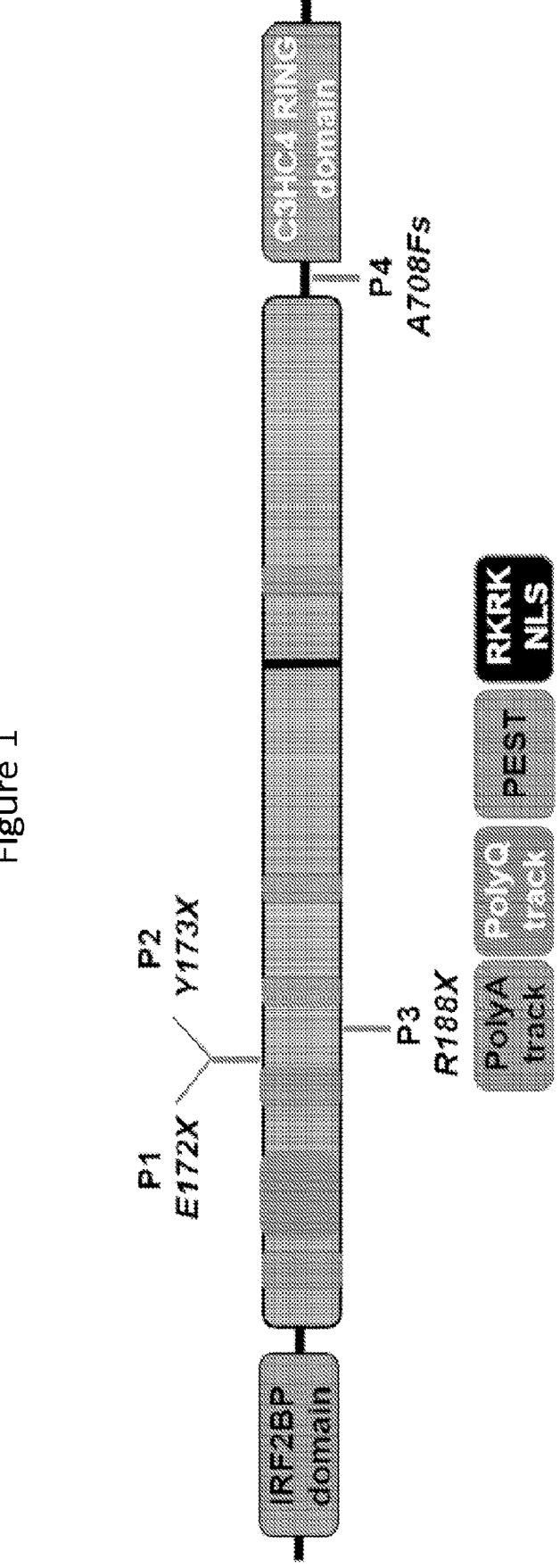
FIG. 1 is a schematic of the IRF2BPL protein domains and the location of the mutations that are present in the patient derived skin fibroblasts used in this study.

Fibroblasts from patients suffering from NEDAMSS (neurodevelopmental disorder with regression, abnormal movements, loss of speech, and seizures) were converted to induced neuronal progenitor cells (iNPCs) as previously described (Meyer et al., PNAS 829-832 (2014)). The fibroblasts were obtained from 4 families having nonsense variants in the IRF2BPL gene resulting in the truncation of its RING finger domain. The IRF2BPL gene mutations represented are summarized below and FIG. 1:

| Family | Mutation | Unaffected family members |
|---|---|---|
| 1 | Proband with E172X and G195V | Unaffected parents |
| 2 | Proband with Y173X variant | Three unaffected family members (parents + sib) |
| 3 | Proband with R188X variant | Unaffected parents |
| 4 | Proband with A708fs variant | Three unaffected family members (parent + sib) |

| Cell Line | Description |
|---|---|
| H1 | Healthy unrelated boy (S3) |
| H2 | Healthy sister (542) |
| H3 | Healthy adult female (AG) |
| H4 | Healthy adult male (fTM154) |
| P1 | Child patient with stop codon mutation near N terminal (537) |
| P2 | Child patient with stop codon mutation near N terminal (152) |
| P3 | Adult patient with stop codon mutation near N terminal (1911) |
| P4 | Child patient with frameshift mutation near C terminal (645) |

Neuronal progenitors' cells were cultured on fibronectin coated dishes in NPC media (DMEM/F12 media containing 1% N2 supplement (Life Technologies), 1% B27, 1% Anti-anti (antibiotic-antimycotic) 20 ng/ml fibroblast growth factor-2) until confluent. iAstrocytes were differentiated by seeding a small quantity of NPCs on another fibronectin coated dish in astrocyte inducing media (DMEM media containing 0.2% N2). These induced astrocytes are referred to as iastrocytes or iAST herein. Five days post differentiation, induced astrocytes were seeded either into a 96 well (10,000 cells/well), 384 well (2,500 cells/well), a 24 well seahorse plate (20,000 cells/well) or a 96 well seahorse plate (10,000 cells/well).

Immunohistochemistry was carried out on the primary fibroblasts from NEDAMSS patients and the iastrocytes from the same patients using an antibody specific for IRF2BPL (Novus Biologics). As shown in FIG. 2, expression of the IRF2BPL protein was not significantly different in the primary fibroblasts from the NEDAMSS patients (P1, P2 and P4) except the cells from patient P3 showed reduced expression, compared to fibroblasts from healthy individuals (H1, H2, H3 and H4). Similarly, as shown in FIG. 3, expression levels of the IRF2BPL protein was similar in the iastrocytes from the NEDAMSS patients and the heathy individuals, except for the cell line from patient P3 which showed significantly lower expression.

FIGS. 4A and B provide representative photos of the immunohistochemistry staining for IRF2BPL (red staining) and DAPI for the cell nucleus (blue), and FIG. 5 provides quantification of the aberrant cytoplasmic accumulation as observed from the immunofluorescence images. The normalized ratio is the number of cells with cytoplasm accumulation of IRF2BPL in astrocytes to the DAPI counts (n=3). Blinded-hand counting was carried out by two independent researchers. There was a clear difference in cytoplasmic IRF2BPL protein localized in patient cell lines. These photos and the graphs provided in FIG. 6 demonstrate that the IRF2BPL accumulated more in the cytoplasm of the iastrocytes derived from the NEDAMSS patients (P1, P2, P3 and P4) rather than localizing mostly to the nucleus of the iastrocytes like the healthy individuals (H1 and H3). NPER extraction kit was used to separate the two extracts and confirmed accumulation of the protein in the cytoplasm in patient astrocytes.

Coculture of iastrocytes with mouse stem cell derived GFP positive motor neurons (according to publication Meyer et al, PNAS 2014). Briefly, iastrocytes were plated in a 96 well plate to form a monolayer. The next day 10K, FACS sorted gfp positive mouse motor neurons are added to each well. Survival and morphology of neurons are monitored using the INCELL6000 automatic imager and analyzer software for 3 days. It was determined that astrocytes from NEDAMSS patients were toxic or less supportive to the motor neurons compared to iastrocytes from healthy controls. FIG. 7A provides representative photos of the motor neurons in the coculture with iastrocytes from NEDAMSS patients and healthy individuals and 7B shows the percentage motor neuron survival. NEDAMSS astrocytes show significantly reduced motor neuron survival in the cocultures compared to healthy astrocytes on day 3. Of note, only the motor neurons are visible as they contain GFP (represented in black). In these photos, the motor neurons are visible due to GFP expression and the iastrocytes are not visible.

FIGS. 8 and 9 demonstrate that the NEDAMSS patients have increased secretion of WNT1 compared to healthy patients. Dysregulation of wnt signaling pathway could lead to neurodegeneration in NEDAMSS patients.

Example 2—Neurons from NEDAMSS Patients have Reduced Survival

Fibroblasts isolated from healthy individuals and NEDAMSS patients were differentiated to neurons as described in Hu et al., Cell Stem Cell, 17(2):204-12., 2015, the disclosure of which is incorporated herein by reference in its entirety. The fibroblasts were incubated with 7 small molecules as described in Hu et al (supra) for 7 days. This method does not use transcriptional factor-expressing virus. FIGS. 10A and B provide representative photos showing that the neurons induced from fibroblasts from NEDAMSS patients had reduced survival or reduced differentiation capacity. FIG. 10A shows staining for the pan-neuron marker Tuj1 from NEDAMSS patients (P1, P2, P3 and P4) and healthy individuals (H1, and H2). FIG. 10B show staining for the neuronal subtype marker Gaba in neurons from NEDAMSS patients (P1, P2 and P3) and a healthy individual (H2). FIG. 11 provides quantification of the number of Tuj1+ neurons (Tuj1) to DAPI and the length of the neurites from the NEDAMSS patients (P1, P2, P3 and P4) and healthy individuals (H1 and H2) on day 7 of differentiation.

Example 3—Constructs Encoding IRF2BPL

The human GFP cDNA clone was obtained from Origene, Rockville, Md. GFP cDNA alone was further subcloned into

Figure 12B:
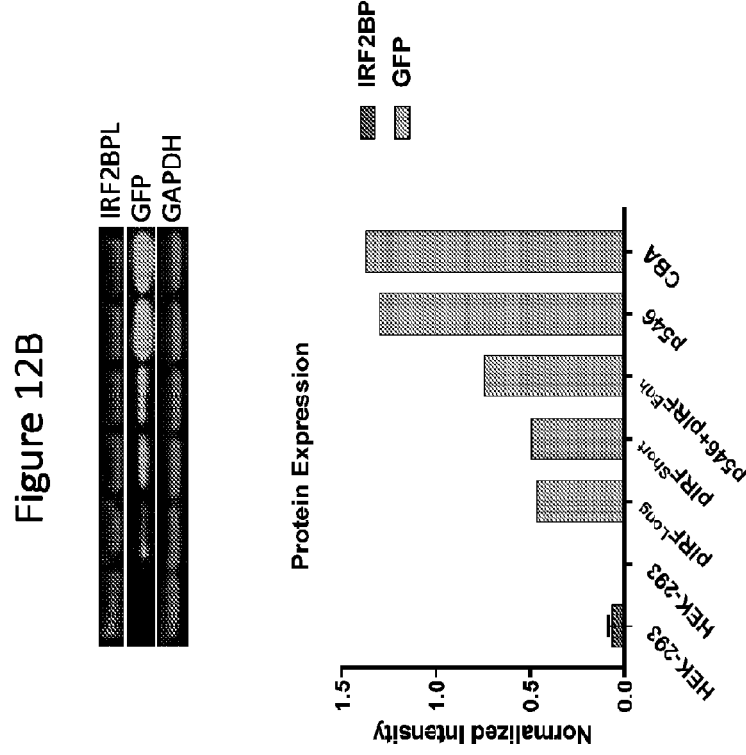

13 a self-complementary AAV9 genome under the control of one or more of either i) 1034 base pair IRF2BPL promoter (pIRF$^{Long}$), ii) 648 base pair fragment of the IRF promoter (pIRF$^{Short}$), iii) or a 296 base pair fragment of the IRF2BPL promoter (pIRF$^{ENH}$), iv) the p546 promoter or v) the hybrid chicken β-Actin promoter (CB). The plasmid construct also included an intron such as the simian virus 40 (SV40) chimeric intron, 907 base pairs of the 5' untranslated region (UTR) of the full length IRF2BPL gene and a Bovine Growth Hormone (BGH) polyadenylation signal (BGH PolyA). The constructs were packaged into an AAV9 genome. These constructs were generated to investigate the regulatory control and strength of the promoters. Briefly, the plasmids were transiently transfected into human embryonic kidney cells using Calcium Phosphate. After incubation of several days, GFP was monitored using microscopes allowing visualization as well as the expression was quantified by qPCR and western blot. FIGS. 12A and 12B provides comparative IRF2BPL mRNA (FIG. 12A) and IRF2BPL (FIG. 12B) expression between wild-type IRF2BPL levels in HEK-293 and GFP levels as induced by the five different promoters.

Exemplary polynucleotide constructs encoding IRF2BPL were generated as set forth in FIG. 13, the AAV9 vector design with the full-length transcript of IRF2BPL under the control of truncated variants of its endogenous promoter. The polynucleotide sequence of ssAAV9-p546+pIRF$^{ENH}$-5'UTR-IRF2BPL is set forth in SEQ ID NO: 3, in which the p546 promoter is followed by the truncated variant of the endogenous promoter pIRF$^{296}$. The polynucleotide sequence of ssAAV9-pIRF$^{SHORT}$-5'UTR-IRF2BPL is set forth in SEQ ID NO: 4 in which the truncated variant of the endogenous promoter is the pIRF$^{648}$. The polynucleotide sequence of ssAAV9-p546-5'UTR-IRF2BPL is set forth in SEQ ID NO: 7 in which the promoter is the p546 promoter. Annotated sequences showing the location of the construct elements are set out in FIGS. 14, 15 and 16 and summarized in the tables below.

| ssAAV9-p546 pIRF$^{ENH}$-5'UTR-IRF2BPL (SEQ ID NO: 3) | |
| --- | --- |
| AAV2 ITR | nucleotides 342-482 |
| p546 promoter | nucleotides 534-1079 |

14

-continued

| ssAAV9-p546 pIRF$^{ENH}$-5'UTR-IRF2BPL (SEQ ID NO: 3) | |
| --- | --- |
| pIRF$^{296}$ | nucleotides 1154-1449 |
| 5'UTR | nucleotides 1456-2362 |
| IRF2BPL | nucleotides 2363-4753 |
| BGHpA | nucleotides 4760-4808 |
| AAV2 ITR | nucleotides 5159-5299 |

| ssAAV9-pSHORT-5'UTR-IRF2BPL (SEQ ID NO: 4) | |
| --- | --- |
| AAV2 ITR | nucleotides 342-482 |
| pSHORT$^{648}$ | nucleotides 534-1182 |
| 5'UTR | nucleotides 1188-2094 |
| IRF2BPL | nucleotides 2095-4985 |
| BGHpA | nucleotides 4492-4540 |
| AAV2 ITR | nucleotides 4891-5031 |

| ssAAV9-p546-5'UTR-IRF2BPL (SEQ ID NO: 7) | |
| --- | --- |
| AAV2 ITR | nucleotides 342-482 |
| p546 promoter | nucleotides 534-1079 |
| 5'UTR | nucleotides 1227-2133 |
| IRF2BPL | nucleotides 2134-4524 |
| BGHpA | nucleotides 4531-4579 |
| AAV2 ITR | nucleotides 4930-5070 |

REFERENCES

Marcogliese et al., IRF2BPL Is Associated with Neurological Phenotypes. The American Journal of Human Genetics, 2018, 103(3).

Meyer et al. Direct conversion of patient fibroblasts demonstrates non-cell autonomous toxicity of astrocytes to motor neurons in familial and sporadic ALS. PNAS, 2014, 2014, 111(2):829-832

Hu et al. Direct Conversion of Normal and Alzheimer's Disease Human Fibroblasts into Neuronal Cells by Small Molecules. Cell Stem Cell, 2015, 17(2):204-12.

What is claimed is:

1. A polynucleotide comprising
   (a) a regulatory control element, wherein the regulatory control element is (i) a pIRF promoter comprising the sequence set forth by SEQ ID NO: 9 or SEQ ID NO: 10, or (ii) a pIRF promoter comprising the sequence set forth by SEQ ID NO: 8 operably linked to a p546 promoter comprising the sequence set forth by SEQ ID NO: 5; and
   (b) an Interferon regulatory factor 2 binding protein like (IRF2BPL) cDNA sequence operably linked to the regulatory control element.

2. The polynucleotide of claim 1, wherein the IRF2BPL cDNA comprises the polynucleotide sequence set forth in SEQ ID NO: 1.

3. A recombinant adeno-associated virus (rAAV) having a genome comprising a polynucleotide sequence of claim 1.

4. The rAAV of claim 3, wherein the genome comprises the polynucleotide of claim 1, wherein the regulatory control element is a pIRF promoter comprising the sequence set forth by SEQ ID NO: 9 and an IRF2BPL cDNA sequence operably linked to the regulatory control element.

5. The rAAV of claim 3, wherein the genome comprises the polynucleotide of claim 1, wherein the regulatory control element is a pIRF promoter comprising the sequence set forth by SEQ ID NO: 10 and an IRF2BPL cDNA sequence operably linked to the regulatory control element.

6. The rAAV of claim 3, wherein the genome comprises the polynucleotide of claim 1, wherein the regulatory control element is a pIRF promoter comprising the sequence set forth by SEQ ID NO: 8 operably linked to a p546 promoter comprising the sequence set forth by SEQ ID NO: 5, and an IRF2BPL cDNA sequence operably linked to the regulatory control element.

7. The rAAV of claim 3, wherein the rAAV is of the serotype AAV1, AAV2, AAV3, AAV4, AAV5, AAV6, AAV7, AAV8, AAV9, AAVRH10, AAVRH74, AAV11, AAV12, AAV13 or Anc80, AAV7m8 and their derivatives.

* * * * *